United States Patent [19]
Castellano et al.

[11] Patent Number: 5,536,249
[45] Date of Patent: Jul. 16, 1996

[54] PEN-TYPE INJECTOR WITH A MICROPROCESSOR AND BLOOD CHARACTERISTIC MONITOR

[75] Inventors: Thomas P. Castellano, Los Angeles; Robert Schumacher, Beverly Hills, both of Calif.

[73] Assignee: Visionary Medical Products, Inc., Los Angeles, Calif.

[21] Appl. No.: 208,636

[22] Filed: Mar. 9, 1994

[51] Int. Cl.$^6$ .................................................. A61M 5/10
[52] U.S. Cl. ........................................ 604/65; 128/DIG. 1
[58] Field of Search ................................. 604/65, 30–34, 604/66–67, 118, 151, 246, 264, 280; 128/DIG. 1, DIG. 12, DIG. 13

[56] References Cited

U.S. PATENT DOCUMENTS

| | | |
|---|---|---|
| 1,997,129 | 4/1935 | Taylor et al. . |
| 2,221,739 | 11/1940 | Reiter . |
| 2,605,763 | 8/1952 | Smoot . |
| 2,632,445 | 3/1953 | Kas . |
| 2,695,023 | 11/1954 | Brown . |
| 2,718,299 | 9/1955 | Atwater et al. . |
| 3,110,310 | 11/1963 | Cislak . |
| 3,141,583 | 7/1964 | Mapel et al. . |
| 3,293,749 | 12/1966 | George et al. . |
| 3,348,545 | 10/1967 | Sarnoff et al. . |
| 3,481,510 | 12/1969 | Allen, Jr. . |
| 3,517,668 | 6/1970 | Brickson . |
| 3,583,399 | 6/1971 | Ritsky . |
| 3,894,663 | 7/1975 | Carhart et al. . |
| 3,977,574 | 8/1976 | Thomas . |
| 4,022,207 | 5/1977 | Citrin . |

(List continued on next page.)

FOREIGN PATENT DOCUMENTS

| | | |
|---|---|---|
| 1103314 | 6/1981 | Canada . |
| 0037696 | 10/1981 | European Pat. Off. . |
| 0058536 | 8/1982 | European Pat. Off. . |
| 0143895 | 6/1985 | European Pat. Off. . |
| 0416975 | 3/1991 | European Pat. Off. . |
| 91225137 | 6/1991 | European Pat. Off. . |
| 93249687 | 6/1993 | European Pat. Off. . |
| 1149735 | 12/1957 | France . |
| 1170312 | 1/1959 | France . |
| 1445659 | 6/1966 | France . |
| 2418642 | 9/1979 | France . |
| 2557445 | 5/1985 | France . |
| 730971 | 12/1942 | Germany . |
| 1070784 | 12/1959 | Germany . |
| 22140 | 10/1961 | Germany . |
| 293302 | 9/1953 | Switzerland . |
| 1225495 | 3/1971 | United Kingdom . |
| 1574267 | 9/1980 | United Kingdom . |
| 2109690 | 2/1982 | United Kingdom . |
| WO8502546 | 6/1985 | WIPO . |
| 8601728 | 3/1986 | WIPO . |
| 9213583 | 8/1992 | WIPO . |

OTHER PUBLICATIONS

Search Report for PCT/US95/02727, mailed Jun. 20, 1995, case claims priority on this U.S. application.
Annual International Conference of the IEEE Engineering in Medicine and Biology Society, "An Optical and RF Telemetry Drug Injection Control and ECG System for Awake Small Animal Studies", vol. 13, No. 5, 1991.
PCT Written Opinion issued by the European Patent Office on Nov. 3, 1995.

Primary Examiner—Manuel Mendez
Attorney, Agent, or Firm—Loeb & Loeb

[57] ABSTRACT

A medical injection device, such as a pen-type injector has a microprocessor coupled to the injector that records the date, the time, and the amount of each injection. The microprocessor may also be coupled to a display to indicate the amount of medication to be injected. The medical injection device can also be coupled with a blood characteristic monitor to analyze characteristics of the blood. This provides a single, all-in-one device that performs a variety of functions, and requires only a minimum of space. The medical injection device may also use a disposable needle that substantially eliminates or reduces bleeding from an opening in the skin at the injection site.

55 Claims, 19 Drawing Sheets

U.S. PATENT DOCUMENTS

| | | | |
|---|---|---|---|
| 4,099,548 | 7/1978 | Sturm et al. . | |
| 4,146,029 | 3/1979 | Ellinwood, Jr. | 128/260 |
| 4,333,458 | 6/1982 | Margulies et al. . | |
| 4,395,921 | 8/1983 | Oppenlander . | |
| 4,413,760 | 11/1983 | Paton . | |
| 4,415,101 | 11/1983 | Shapiro et al. . | |
| 4,425,121 | 1/1984 | Young et al. . | |
| 4,435,173 | 3/1984 | Siposs et al. | 128/DIG. 1 |
| 4,444,560 | 4/1984 | Jacklich . | |
| 4,457,712 | 7/1984 | Dragan . | |
| 4,470,317 | 9/1984 | Sabloewski et al. . | |
| 4,475,905 | 10/1984 | Himmelstrup . | |
| 4,498,904 | 2/1985 | Turner et al. . | |
| 4,526,294 | 7/1985 | Hirschmann et al. . | |
| 4,529,401 | 7/1985 | Uslie et al. | 128/DIG. 1 |
| 4,581,022 | 4/1986 | Leonard et al. . | |
| 4,592,745 | 6/1986 | Rex et al. | 604/211 |
| 4,659,327 | 4/1987 | Bennett et al. . | |
| 4,664,128 | 5/1987 | Lee . | |
| 4,710,172 | 12/1987 | Jacklich et al. . | |
| 4,710,178 | 12/1987 | Leonard et al. . | |
| 4,820,287 | 4/1989 | Leonard . | |
| 4,865,591 | 9/1989 | Sams . | |
| 4,883,472 | 11/1989 | Michel | 604/208 |
| 4,936,833 | 6/1990 | Sams | 604/232 |
| 4,950,246 | 8/1990 | Muller | 604/154 |
| 4,959,056 | 9/1990 | Dombrowski et al. | 604/186 |
| 4,998,570 | 3/1991 | Strong | 128/DIG. 1 |
| 5,024,656 | 6/1991 | Gasaway et al. | 604/70 |
| 5,069,668 | 12/1991 | Boydman | 604/121 |
| 5,085,642 | 2/1992 | Sarnoff et al. | 604/134 |
| 5,092,842 | 3/1992 | Bechtold et al. | 604/135 |
| 5,102,393 | 4/1992 | Sarnoff et al. | 604/136 |
| 5,104,380 | 4/1992 | Holman et al. | 604/117 |
| 5,112,317 | 5/1992 | Michel | 604/208 |
| 5,114,406 | 5/1992 | Gabriel et al. | 604/136 |
| 5,139,484 | 8/1992 | Hazon et al. | 128/DIG. 1 |
| 5,180,371 | 1/1993 | Spinallo | 604/207 |
| 5,226,895 | 7/1993 | Harris | 604/208 |
| 5,226,896 | 7/1993 | Harris | 604/211 |
| 5,244,461 | 9/1993 | Derlien | 128/DIG. 1 |
| 5,244,465 | 9/1993 | Michel | 604/208 |
| 5,279,585 | 1/1994 | Balkwill | 604/207 |
| 5,279,586 | 1/1994 | Balkwill | 604/207 |
| 5,383,865 | 1/1995 | Michel | 604/208 |

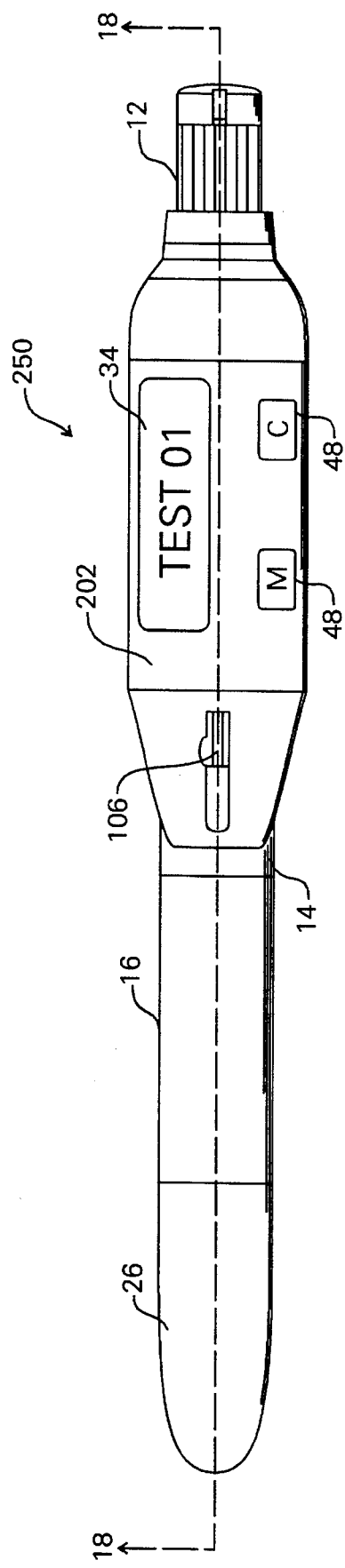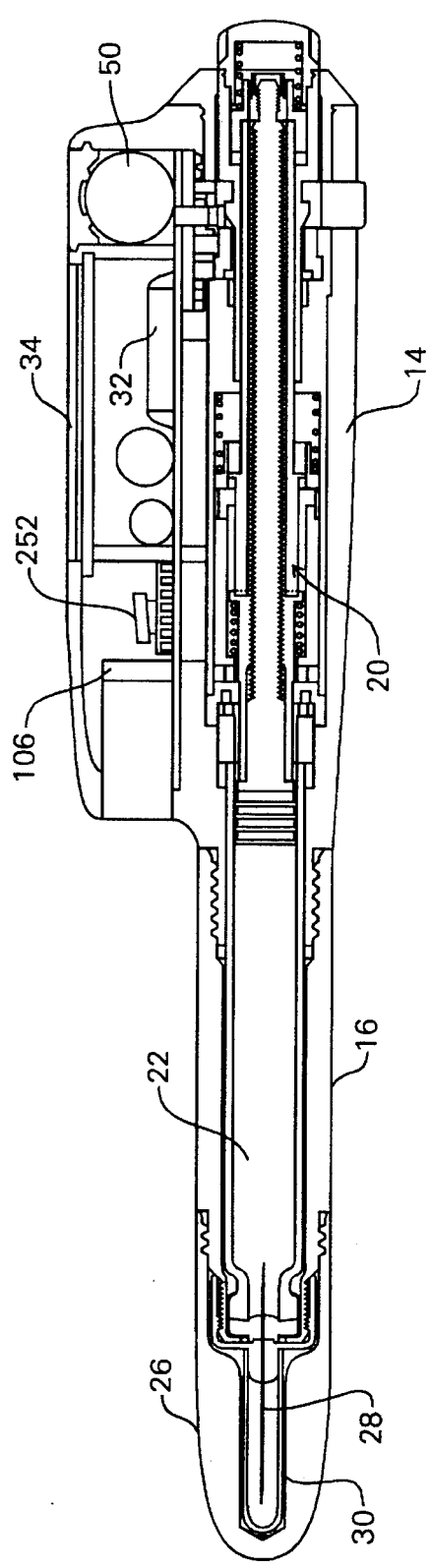
FIG. 17
FIG. 18

BLOOD GLUCOSE (mg/dL) INSULIN LOG

| Name: Good, Johnny B.  <br>I.D. or Chart #  <br>Phys/Inst: Cedars S. | Report Date: 12-31-93  <br>Report Time: 13:50  <br>Report Span: 12-24 to 12-30-93 | | | | | | |
|---|---|---|---|---|---|---|---|
| | Breakfast | | Lunch | | Dinner | | Snack |
| | Pre | Post | Pre | Post | Pre | Post | |
| No. of Readings | 7 | 0 | 7 | 0 | 7 | 0 | 7 |
| Std. Deviation | 51.0 | | 42.0 | | 61.0 | | 29.0 |
| Average | 99.3 | | 113.4 | | 130.4 | | 86.0 |

FIG. 24(a)

Blood Glucose Chart:

| | BLOOD GLUCOSE | | | | | | | |
|---|---|---|---|---|---|---|---|---|
| | Breakfast | | Lunch | | Dinner | | Snack | Other |
| | Pre | Post | Pre | Post | Pre | Post | | |
| 12-24-93 Fri | 06:30 190 | | 11:24 101 | | 16:41 122 | | 21:25 77 | |
| 12-25-93 Sat | 06:41 47 | | 11:20 146 | | 16:20 137 | | 21:15 123 | |
| 12-26-93 Sun | 06:30 59 | | 11:25 113 | | 16:36 156 | | 21:30 111 | |

FIG. 24 (b)

Insulin Chart:

| | INSULIN | | | |
|---|---|---|---|---|
| | Breakfast | Lunch | Dinner | Evening |
| 12-24-93 Fri | 06:39 R-3 L-7 | 11:38 R-6 L-6 | 16:56 R-13 L-11 | 21:37 R-7 L-12 |
| 12-25-93 Sat | 06:42 R-2 L-5 | 11:24 R-3 L-6 | 16:30 R-10 L-10 | 21:33 R-6 L-10 |
| 12-26-93 Sun | 06:36 R-4 L-6 | 11:30 R-6 L-6 | 16:40 R-8 L-12 | 21:40 R-8 L-10 |

FIG. 24 (c)

Markers Chart:

| | MARKERS | | | |
|---|---|---|---|---|
| | Symptom | Meal | Exercise | Special |
| 12-24-93 Fri | | 17:15 inc | | |
| 12-25-93 Sat | 06:00 | | 18:30 | |
| 12-26-93 Sun | | | 18:15 inc | |

FIG. 24 (d)

PEN-TYPE INJECTOR WITH A MICROPROCESSOR AND BLOOD CHARACTERISTIC MONITOR

FIELD OF THE INVENTION

This invention relates to pen-type injectors for injecting medications or other injectable substances and, in particular embodiments, a pen-type injector for injecting insulin. In preferred embodiments, the pen-type injector utilizes a microprocessor to record injection information and a monitor to measure blood characteristics. Further embodiments of the invention also relate to blood characteristic monitors that are incorporated into wrist watches.

BACKGROUND OF THE INVENTION

Home treatment methods for the control and management of various diseases are becoming more popular. For instance, high success rates for treatment of diabetes have been achieved when a diabetic patient controls the disease by self-testing blood glucose levels and administering a correct dose of insulin. The doctor works with the patient to determine the best regimen of diet, exercise, and insulin dose to maintain a target blood glucose level.

Between doctor's office visits, the patient is responsible for carrying out the prescribed regimen, which includes frequent blood testing and insulin administration using a syringe, needleless injector, pen-type injector or insulin pump. The patient and doctor select a blood glucose monitor based on desired monitor features, suitability for the patient, perceived accuracy, and ease of use.

Home diabetes therapy requires personal discipline of the user, is time consuming, requires an appropriate location, and the proper instruments and accessories. Therefore, it is highly desirable that the home therapy regimen cause minimal inconvenience and changes in the patient's lifestyle. Many past therapy regimens and devices have failed to provide the convenience and minimum changes to the patient's lifestyle, and thus the compliance with the medical regimens have been less than satisfactory.

Traditionally, for out-patient and in-home patient care, medication has been injected by a syringe, wherein the user has to insert the needle of the syringe into a separate medication vial to withdraw medication. Once the medication is withdrawn from the vial, the user removes any air bubbles and extra medication, and then injects the medication.

Typical syringes suffer from many drawbacks. For instance, they may not be preloaded with medication; thus, requiring the user to carry a separate medication vial. Moreover, people with dexterity disorders often have difficulty lining up the needle portion of the syringe with the rubber septum on the medication vial. This can lead to unintentional needle pricks or excessive time being required to complete an injection, both of which tend to inhibit compliance with a medical regimen. Also, it is often difficult for children or people with failing eyesight to line up the medication with the proper dosage line on the outer casing of the syringe. Furthermore, the user of the syringe is typically responsible for manually recording the date, the time and the dosage in a separate log book so that the doctor can monitor the user's compliance with the prescribed medical regimen.

Another drawback to the traditional syringe is that a syringe is difficult to use in public places. For instance, many schools do not allow students to carry syringes. This prohibition against syringes can cause excessive delays between injections, and thus could complicate a user's medical condition. Moreover, there is also a social stigma attached to using a syringe, since it raises connotations of drug abuse. These drawbacks have been one of the principal reasons why users have abandoned medical regimens requiring the use of syringes in social settings.

As an alternative, pen-type injectors have been developed. The pen-type injectors often use prepackaged insulin. However, these devices have been inherently inaccurate and undependable due to their difficult to read scales and inadequately designed mechanical injection systems. For example, typical pen-injectors require multiple and repeated activations of the injector mechanism to administer a desired dosage. Thus, during administration of an injection, the user must keep track of the number of activations (i.e., depressions) to determine when the required dosage has been delivered.

Another disadvantage to pen-type injectors is that typical disposable needles used on pen-type injectors cause bleeding during the administration of an injection. This results from the disposable needle spreading the opening in the skin at the injection site, thereby allowing the skin to bleed. This bleeding from traditional disposable needles can discourage users from following the medical regimen, and the bleeding also increases the likelihood of spreading infectious diseases.

Often a user who takes certain medications, such as insulin, in a home therapy regimen must also monitor the level of glucose present in the blood at periodic intervals. The test results are used to determine when another injection should be taken or to determine how the user is responding to prior injections. Typically, the blood monitor is a separate device that the user must carry along with the insulin injector or syringe. To use the blood monitor the user must lance a portion of the body (i.e., typically a finger) and take a sample that is analyzed by the monitor. The user then manually records the results, the time and the date in a separate log book.

SUMMARY OF THE DISCLOSURE

According to embodiments of the present invention, a medical injection device, such as a pen-type injector or the like, has a processor coupled to the injector that records the date, the time, and the amount of each injection. The processor may also be coupled to a display to indicate the amount of medication to be injected.

In particular embodiments, a medical injection device includes an injection mechanism that has an actuator for setting the dosage and administering an injection of a medication contained within the injection device. The injection device also has a processor coupled to the actuator of the injection mechanism to determine a value equal to the dosage set by the actuator of the injection mechanism, and a memory device coupled to the processor to store the value determined by the processor. In further embodiments, the injection device also has a receptacle capable of holding the medication and the injection mechanism further includes a drive mechanism coupled between the actuator and the receptacle to inject the set dosage of the medication. In other embodiments, the injection device also includes a display device to display the value equal to the dosage determined by the processor and a clock circuit for determining the time. In preferred embodiments, the injection device includes a data port for transferring information to and from the processor and memory device to an external device.

In particular embodiments of the present invention, a medical device includes a pen-type injector that is also coupled with a blood characteristic monitor to analyze characteristics of the blood. This provides a single, all-in-one device that performs a variety of functions, and requires only minimal space.

In particular embodiments, a medical device includes a medication injector for injecting a dosage of a medication, a blood characteristic monitor for analyzing a blood sample, and a processor coupled to the medication injector and the blood characteristic monitor. The processor determines a value equal to the dosage of the medication to be injected by the medication injector. The processor also determines blood characteristics from a blood sample analyzed by the blood characteristic monitor.

In further embodiments, the medical device also includes a memory device coupled to the processor to store the value equal to the dosage and the blood characteristics determined by the processor. In preferred embodiments, the medical device includes a data port for transferring information to and from the processor and memory device to an external device and a clock circuit for tracking the time.

According to another embodiment of the invention, a pen-type injector utilizes a disposable needle that substantially eliminates or reduces bleeding from an opening in the skin at the injection site. Also in other embodiments, the pen-type injector uses a direct drive mechanism for injecting the medication with a single depression of an actuator knob. Moreover, the actuator knob is rotatable to adjust the amount of medication that is injected.

In particular embodiments, a disposable needle for a pen-type injector has a base adapted to be coupled to a pen-type injector, an injection needle having a injection end and a connecting end, and a hollow cylindrical cover having an open end and an opposite connecting end. Both the connecting end of the injection needle and the opposite connecting end of the hollow cylindrical cover are coupled to the base such that the injection needle is disposed in the center of the open end of the hollow cylindrical cover with the connecting end of the injection needle inside the hollow cylindrical cover below the open end of the hollow cylindrical cover. Moreover, the injection end of the injection needle extends beyond the open end of the hollow cylindrical cover.

According to a further embodiment of the present invention, a watch monitor includes a blood characteristic monitor and a clock that performs as a wrist watch. The watch monitor utilizes a high quality blood analysis device that can record detailed information on blood analysis results and injections. Moreover, the device can be worn easy and unobtrusively on a wrist so that typical time and alarm functions are combined with the blood characteristic monitor to coordinate the blood testing regimen and reduce the number of items a user must carry. Thus, a user has improved detailed record keeping, regimen alarms and reminders, blood characteristic analysis capabilities, and time keeping functions in a single, all-in-one device.

In particular embodiments of the present invention, a portable blood monitor includes a housing of suitable size and configuration to be worn on a wrist, a clock contained in the housing for measuring time, and a blood characteristic monitor contained in the housing for analyzing a blood sample. The portable blood monitor also includes a processor coupled to the blood characteristic monitor and the clock. The processor determines blood characteristics based on the analyzed blood sample from the blood characteristic monitor, and the processor uses the measure of the time from the clock to identify when the blood characteristics were determined. In further embodiments, the portable blood monitor also includes a memory storage device coupled to the processor for storing the measure of time from the clock and the blood characteristics determined by the processor, and a display device to display the measure of the time from the clock and the blood level characteristics determined by the processor. In preferred embodiments, the portable blood monitor includes a data port for transferring information to and from the processor and memory device to an external device and the data port may utilize infrared communication technology to transfer the information.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 17 shows a top view of another pen-type injector with a blood characteristic monitor in accordance with an embodiment of the present invention.

FIG. 18 is a cross-sectional view of the pen-type injector with a blood characteristic monitor as shown along the line 18—18 in FIG. 17.

FIGS. 24(a)–24(d) are diagrams of typical reports obtained from the embodiment shown in FIGS. 22 and 23.

DETAILED DESCRIPTION OF THE PREFERRED EMBODIMENTS

Figure 1:
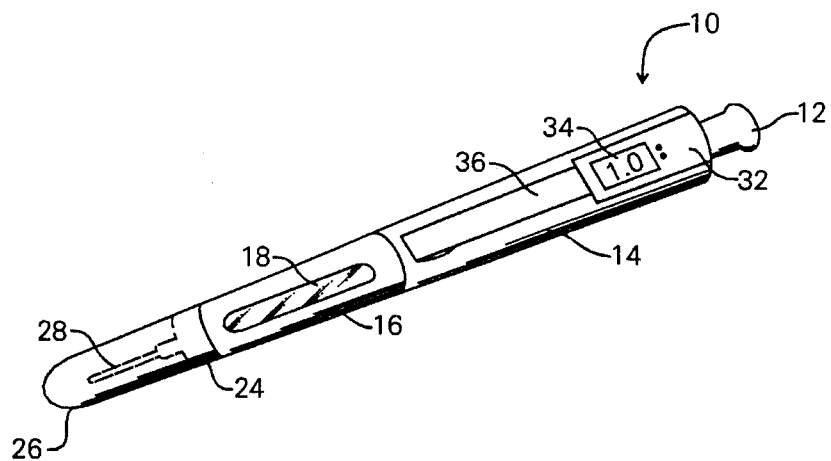
FIG. 1 is a perspective view of a pen-type injector in accordance with an embodiment of the present invention.

As shown in the drawings for purposes of illustration, the invention is embodied in a pen-type injector utilizing a microprocessor. In particular embodiments of the present invention, the pen-type injector further includes a blood characteristic monitor to measure characteristics of a blood sample. In further embodiments, the pen-type injector uses a direct drive injection mechanism, and may include a disposable needle which substantially eliminates or reduces bleeding caused from administration of an injection. In other embodiments, a blood characteristic monitor is contained within a wrist watch sized device that combines blood characteristic monitoring, time keeping and information recording in a single, all-in-one device that is worn on a user's wrist.

In preferred embodiments of the present invention, the pen-type injector is used to inject insulin, and the blood characteristic monitor is used to determine the amount of glucose present in a blood sample. However, it will be recognized that further embodiments of the invention may be used with other types of medication or other injectable substances, such as vitamins, growth hormones or the like. Moreover, embodiments of the present invention may be used with other types of injectors that are not pen shaped, such as jet injectors and the like. Furthermore, in other embodiments, the blood characteristic monitor may be used to monitor other characteristics, such as hormone levels, cholesterol levels or the like.

Embodiments of the present invention combine pen-type injectors with a microprocessor to accurately set and determine the dosage of a medication that is injected into the user. Moreover, the microprocessor serves to record important information concerning the injection, such as the date, the time and the amount of medication injected. This information is displayed on an LCD display, or the like, for easy review by the user or doctor. This allows the user to carry one self-contained injection device that does not require carrying a separate medication vial and syringes, since the vial is contained within the injector. Moreover, the user does not have to carry a separate log book to record relevant and required information concerning the injection, since this information is automatically recorded by the microprocessor for later recall.

A preferred embodiment of the pen-type injector has a direct drive injection mechanism for accurate dosing and ease of use. The drive utilizes a rotatable dosage knob provided at one end of the pen-type injector. The dosage knob allows the user to accurately adjust the amount of medication or insulin that will be injected by the pen-type injector, since rotating the dosage knob limits the distance that the dosage knob can be depressed. Accuracies of 0.001 to 0.01 ccs (0.1 to 1.0 units) can be readily achieved. To inject a dose of medication, the user inserts the needle under the skin and depresses the dosage once knob once as far as it will depress.

In preferred embodiments, the pen-type injector is also combined with a blood characteristic monitor that determines the level of medication in a blood sample. The blood characteristic monitor uses the microprocessor in the pen-type injector (although a separate microprocessor could be used) to process the blood sample results and to store relevant information about the results. Thus, a single, all-in-one device provides medication injection, blood characteristic monitoring, and record keeping. Therefore, a user is only required to carry a single device, and is not required to carry a large number and variety of items to comply with their medical regimen. For example, a separate medication vial, a separate medication injector, a separate blood characteristic monitor and a separate log book are not needed.

In other embodiments, the pen-type injector utilizes a disposable needle that minimizes or substantially eliminates the bleeding that may occur from administering an injection. The disposable needle includes a protective, hollow cylindrical cover that prevents the user from pushing the needle too deeply into the skin. Moreover, the hollow cylindrical cover tends to press the skin together during the administration of an injection to restrict and substantially eliminate bleeding during the injection.

In another preferred embodiment of the present invention, a portable blood monitor combines a blood characteristic monitor with a wrist watch. The blood characteristic monitor is coupled to a microprocessor to analyze blood samples and record relevant data for later recall. The wrist watch performs time keeping functions and provides alarms to notify the user when to monitor blood characteristics and when to administer injections. In particular embodiments, the portable blood monitor has a plurality of keys that allow the user to input additional information concerning injections and special events. In other embodiments, the portable blood monitor includes a data input and output port to provide the capability of programming the portable blood monitor through an external computer, such as a PC, lap top or the like, and to provide for the capability to download the stored information to an external computer for detailed review and analysis by the user or doctor.

Figure 2:
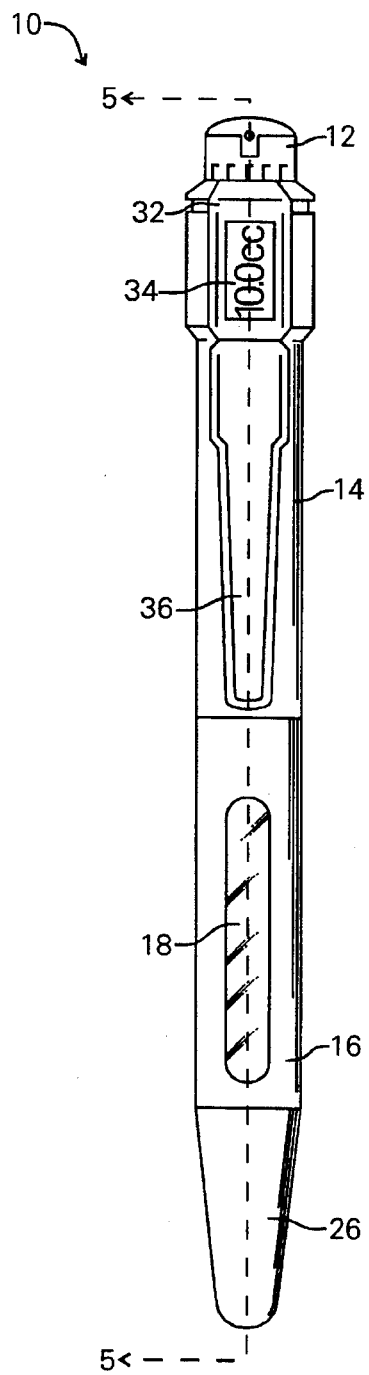
FIG. 2 is a front perspective view of the embodiment of the pen-type injector shown in FIG. 1.
Figure 3:
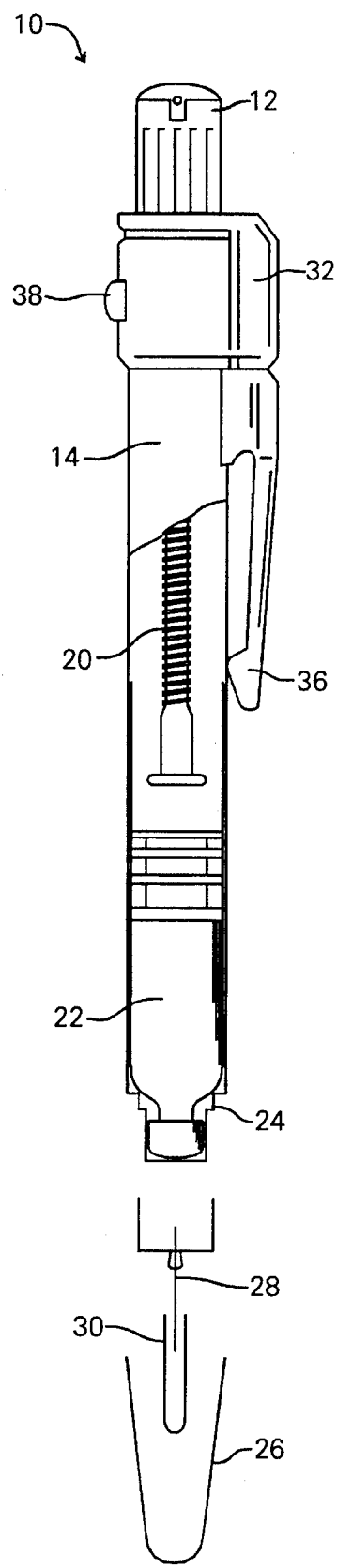
FIG. 3 is a partial cross-sectional and exploded side view of the pen-type injector shown in FIG. 2.

FIGS. 1–3 show a pen-type injector 10 with a microprocessor 32 in accordance with an embodiment of the present invention. The pen-type injector 10 includes a rotatable actuator dosage knob 12, an injection housing 14, and a medication cartridge housing 16 having a view window 18. The actuator knob 12 is coupled to one end of the injection housing 14, and is also operatively coupled to an injection mechanism 20 (see FIG. 3) that is contained within the injection housing 14. The medication cartridge housing 16 is sized to hold a medication cartridge 22 (see FIG. 3) and is coupled to the other end of the injection housing 14 so that the injection mechanism 20 is operatively coupled to the medication cartridge 22. In preferred embodiments, the medication cartridge housing 16 is coupled to the injection mechanism housing 14 by threads, and the medication cartridge 22 is connected to the medication cartridge housing 16 by threads, a friction fit or the like. In particular embodiments, the medication cartridge 22 contains 1.5 ccs (150 units); however, medication cartridges containing more or less medication may be used. In preferred embodiments, the medication cartridge 22 is a Novolin® cartridge by Novo Nordisk Pharm, Inc. or an insulin cartridge by Eli Lilly, Inc.

The view window 18 of the medication cartridge housing 16 allows the user to view the interior contents of the medication cartridge 22. Thus, a user can visually determine when a medication cartridge 22 needs to be replaced with a refill medication cartridge 22, or the user can visually determine the type of medication that is currently contained in the medication cartridge housing 16.

Coupled to the other end of the medication cartridge housing 16 is a needle base 24 for holding a protective needle cover 26 and a disposable needle 28. The needle cover 26 and the disposable needle 28 are detachably coupled to the needle base 24 by threads, friction or the like. The protective needle cover 26 prevents needle pricks until an injection is to be administered. The use of a disposable needle 28 reduces the chances of spreading infections and allows the pen-type injector to be used multiple times. In preferred embodiments, the disposable needle 28 also includes a protective needle sheath 30 to further reduce the likelihood of unintended needle pricks. In particular embodiments, the pen-type injector uses a 27 gauge disposable needle 28; however, other gauges may be used.

Also attached to the injection mechanism housing 14 is a microprocessor 32, a display 34 and a clip 36. The microprocessor 32 accurately determines the dosage of the medication to be injected based upon the rotations of the actuator knob 12 by the user. The microprocessor 32 provides the dosage information to the display 34 to inform the user of the amount of medication that will be injected. In particular embodiments, the display 34 may include a set of user actuatable buttons to set various parameters in the microprocessor, such as the time, the date or the like. The clip 36 attached to the injection mechanism housing 14 provides the capability for the pen-type injector 10 to be carried around like a traditional ball point pen. For example, the pen-type injector 10 can be carried unobtrusively in a shirt pocket or on a clip board.

As shown in FIG. 3, the injection mechanism housing 14 also includes a start button 38. The start button 38 releases the actuator knob 12 from the position shown in FIGS. 1–2 to the released position shown in FIG. 3. The start button 38 locks the actuator knob 12 in the depressed position to prevent accidental discharges of the medication until an injection is to be administered. The start button 38 also activates the microprocessor 32 only when the microprocessor 32 is needed, and this reduces the overall power consumption characteristics of the device.

In preferred embodiments, the actuator knob 12, the injection housing 14, the medication cartridge housing 16, the needle base 24, the protective needle cover 26, and the start button 38 are formed from a plastic material. However, in alternative embodiments, some or all of these parts may be formed from metals, ceramics or other suitable materials. In preferred embodiments, the view window 18 is formed from plastic; however, glass may be used in alternative embodiments. In preferred embodiments, the display 34 is an LCD display; however, in other embodiments, the display may use fluorescent elements, LEDs or the like.

Figure 4:
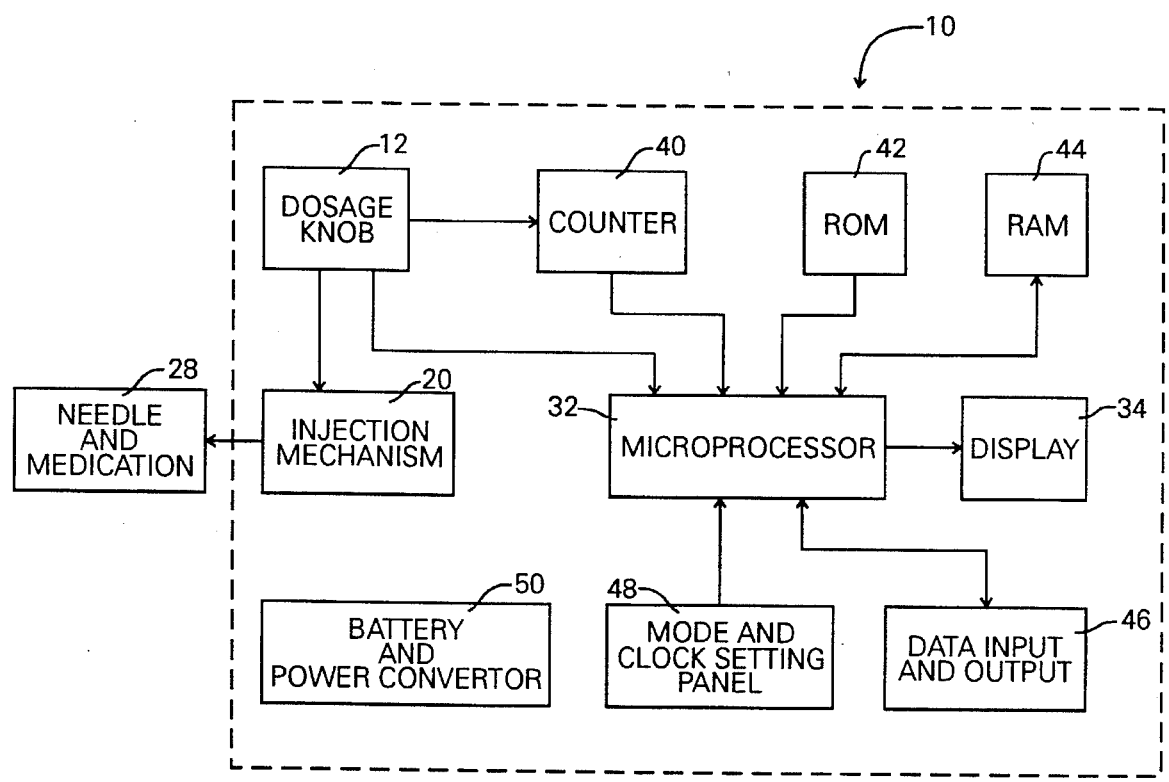
FIG. 4 is a simplified flow block diagram for the pen-type injector as shown in FIG. 1.

FIG. 4 illustrates a simplified flow block diagram of the pen-type injector 10 shown in FIGS. 1–3. The actuator dosage knob 12 is rotated to adjust the injection mechanism 20 and set the dosage of the medication to be injected by the disposable needle 28. In preferred embodiments, the actuator knob 12 can be rotated in two directions to both increase or decrease the dosage level. The actuator knob 12 is coupled to a counter 40 that keeps track of the incremental rotations of the actuator knob 12 and injection mechanism 20. In particular embodiments, the counter 40 is an electronic counter, and in preferred embodiments the electronic counter is bi-directional and can increment and decrement the dosage level. The counter 40 is coupled to the microprocessor 32 to provide the current count in the counter 40 to the microprocessor 32. The current count from the counter 40 is converted into a value equal to the dosage of the medication that will be administered by an injection. The actuator knob 12 is also coupled directly to the microprocessor 32 to activate the microprocessor 32. Thus, when the start button 38 releases the actuator knob 12, the microprocessor 32 is prepared to store relevant information concerning the injection. For instance, the microprocessor 32 will store, the time, the date and the amount of medication injected by the user.

The microprocessor 32 is coupled to a ROM 42 and a RAM 44. In preferred embodiments, the ROM 42 is an EPROM and the RAM 44 is a static RAM; however, other comparable memory storage components may be used. The ROM 42 stores the programs used by the microprocessor 32 to determine various parameters, such as the amount of medication to be injected based upon the count from the counter, the date and the time, and how to report information to the user. The RAM 44 is used by the microprocessor 32 to store information about the injection for later recall by the user or the doctor. For example, a user or doctor can transcribe the stored information at a later time to determine compliance with the medical regimen. This is accomplished by downloading the information to the display 34 and then transcribing all of the stored records at one time as they appear on the display 34.

In preferred embodiments, the microprocessor 32 is coupled to a data input and output (I/O) port 46, and the user can download the stored information to an external computer (not shown) through the data I/O port 46. The data I/O port 46 is capable of transferring data in both directions so that updated program instructions or reminder alarms can be set by the user or doctor.

Also coupled to the microprocessor 32 is a mode and clock setting panel 48 that provides the user with the capability to store additional information, set the date and the time, or set alarms to indicate when to take the next injection. The panel 48 is used in conjunction with the display 34 to access the various modes and alarms utilizing methods typically employed to set the time on an LCD watch or the like.

The pen-type injector 10 also includes a self contained battery and power convertor 50. The battery is a small watch type battery, or in preferred embodiments, the battery is a lithium battery capable of providing power for up to 5 years.

Operation of the embodiment shown in FIGS. 1–4 is relatively simple. The user prepares the pen-type injector 10 by depressing the start button 38 to activate the microprocessor 32. If a new medication cartridge 22 is required, the user unscrews the medication cartridge housing 16 from the injection mechanism housing 14, and couples a pre-filled medication cartridge 22 to the injection mechanism 20 and the injection mechanism housing 14. Once the medication cartridge 22 is attached, the user rescrews the medication cartridge housing 16 onto the injection mechanism housing 14. Next, the user removes the protective needle cover 26, and attaches a disposable needle 28 to the needle base 24. The user then holds the pen-type injector 10 with the disposable needle 28 pointing upward and rotates the actuator knob 12 to set a small amount of medication (typically 2–4 units). The user then depresses the actuator knob 12 to eliminate the small amount of medication and remove the air from the disposable needle 28. Depression of the actuator knob 12 also turns off the microprocessor 32 and prevents accidental discharge of the medication until an injection is to be administered. Finally, the user reattaches the protective needle cover 26 to prevent inadvertent needle pricks or damage to the disposable needle 28.

To give an injection with the pen-type injector 10, the user removes the protective needle cover 26 and, if present, the protective needle sheath 30. The actuator knob 12 is released and the microprocessor 32 is activated by depressing the start button 38. In preferred embodiments,, when activated, the microprocessor 32 displays the time and the amount of the last injection on the display 34 in an alternating sequence for 5 seconds (although longer or shorter periods may be used) to remind the user of the last injection event. This substantially reduces the chance of "double dosing" (i.e., taking too much medication). After the reminder display, the pen-type injector 10 automatically zeros itself so that the user can dial in and set the dosage by rotating the actuator knob 12 in one direction (typically clockwise) until the desired amount of the medication to be injected is displayed on the display 34. In particular embodiments, the display 34 changes in real time, and in preferred embodiments, an audible click or beep is heard as the user rotates the actuator knob 12. Also in preferred embodiments, each click represents an incremental change in the dosage selected (i.e., 0.1, 0.25, 0.5 or 1.0 units). In bi-directional models, the user can increase or decrease the amount of medication to be injected. However, the microprocessor 32 will not allow the user to set a dosage below zero or to select a dosage larger than the amount of medication remaining in the medication cartridge 22.

After the dosage is selected, the user chooses an injection site, pushes the disposable needle 28 under the skin and depresses the actuator knob 12 down as far as it will go. The actuator knob 12 automatically locks in the depressed position when the actuator is depressed completely and the injection is completed. When the actuator knob 12 is depressed, the microprocessor 32 stores the injection event in the RAM 44 by the date, the time and the amount of injected medication. When the user returns home or after a certain number of injections have been administered, the user can activate the microprocessor 32 with the mode and clock setting panel 48 to review the recorded data as it is displayed on the display 34. The patient can transcribe this information in a separate log book if desired. When the user visits the doctor, the doctor can download all the stored injection information into an external computer via the data I/O port 46. The doctor can then review the data to spot trends and determine compliance with the medical regimen. If required, the doctor can update the program instructions in the pen-type injector 10 via the data I/O port 46 to provide reminder alarms at various times.

Figure 5:
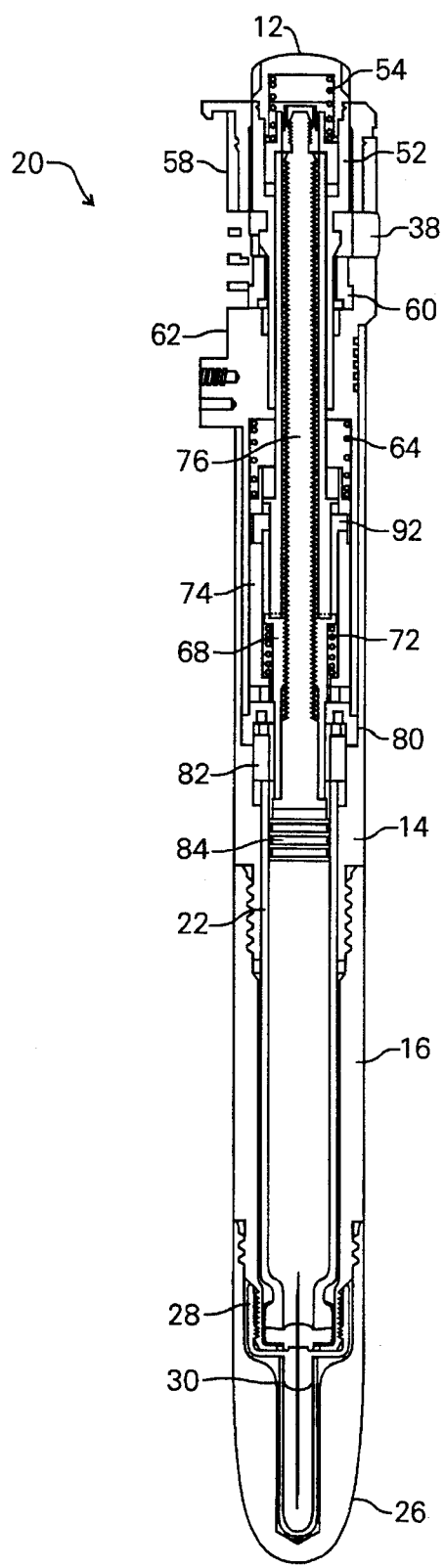
FIG. 5 is a cross-sectional view of the pen-type injector embodiment as shown along the line 5—5 in FIG. 2.
Figure 6:
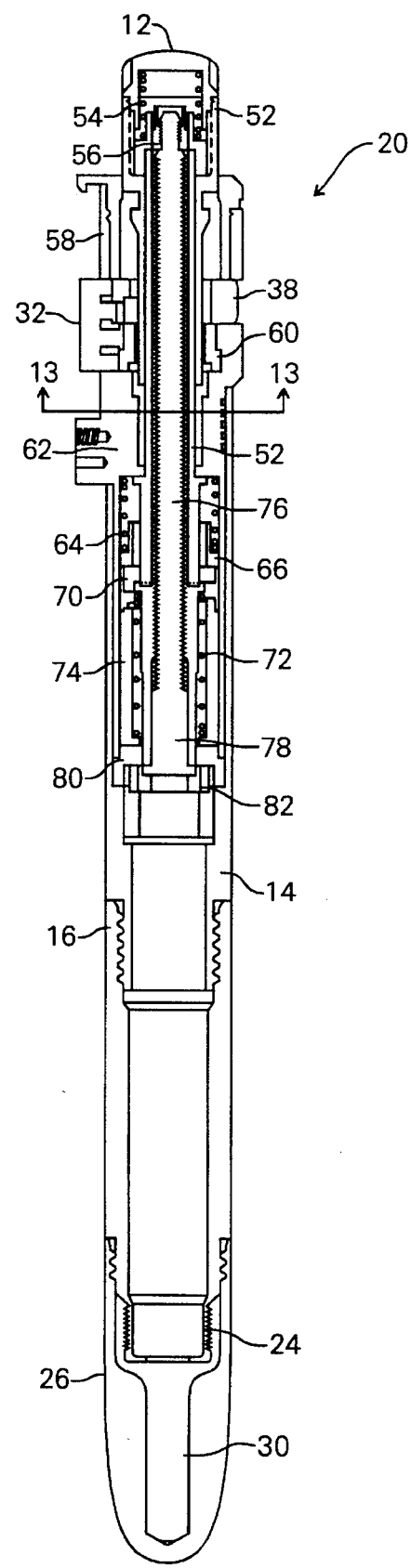
FIG. 6 is another cross-sectional view of the pen-type injector shown in FIG. 5, with the actuator in the released position.
Figure 7:
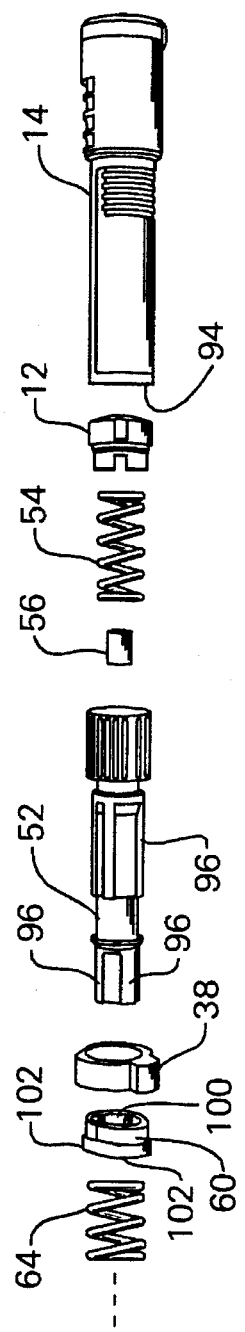
FIGS. 7–12 show various perspective views of a drive mechanism in accordance with an embodiment of the present invention.
Figure 7:
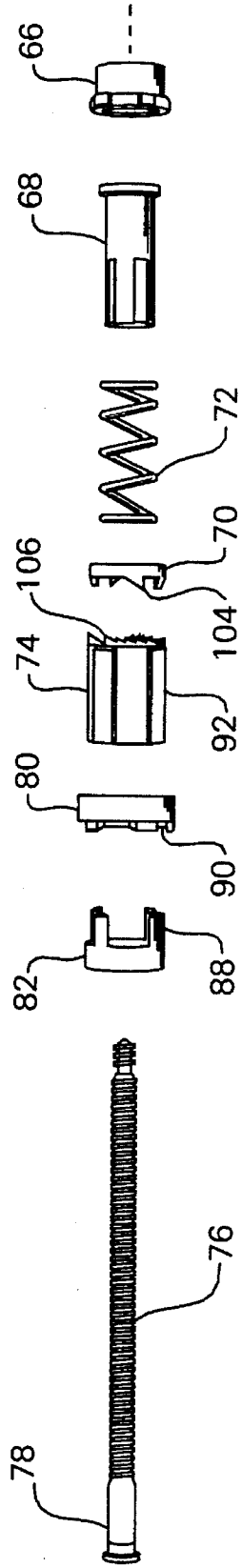
Figure 8:
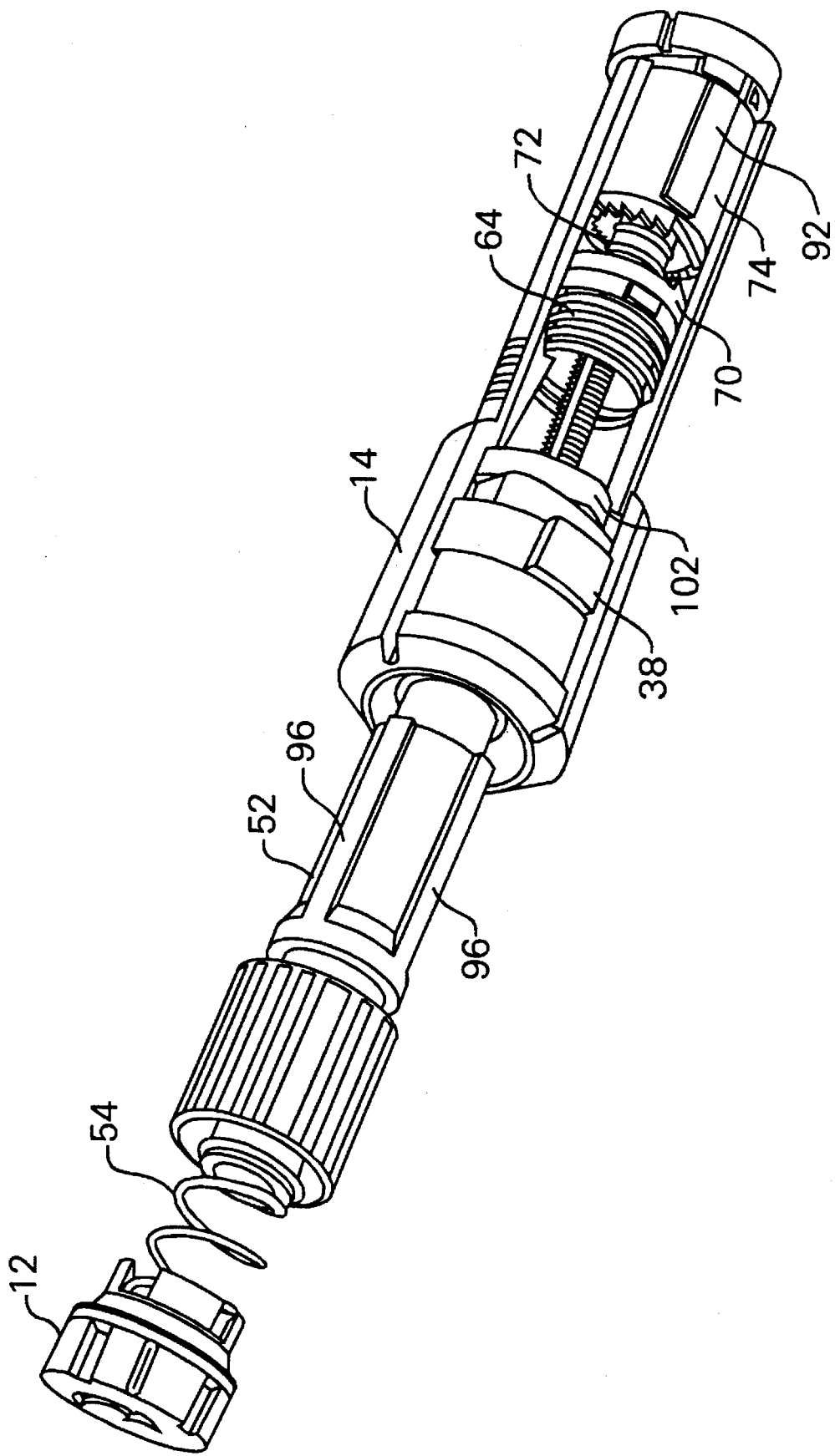
Figure 9:
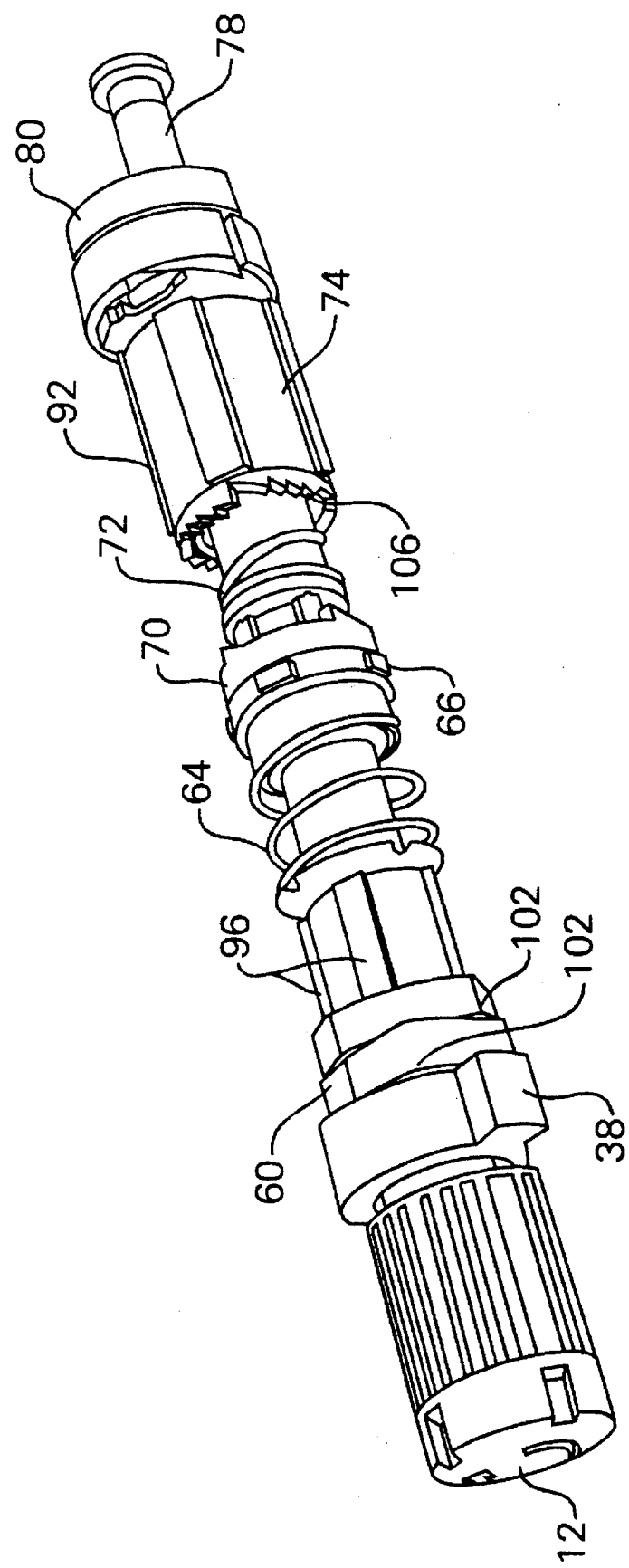
Figure 10:
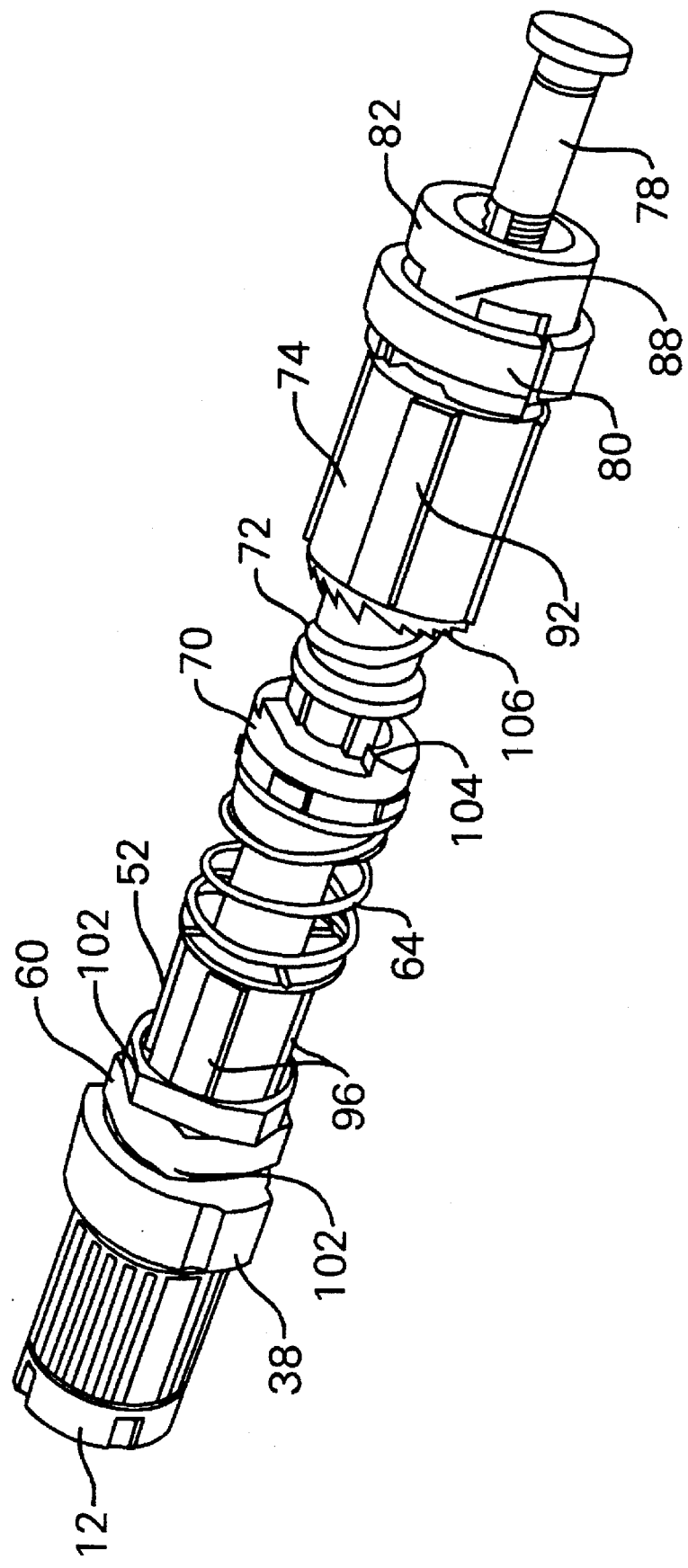
Figure 11:
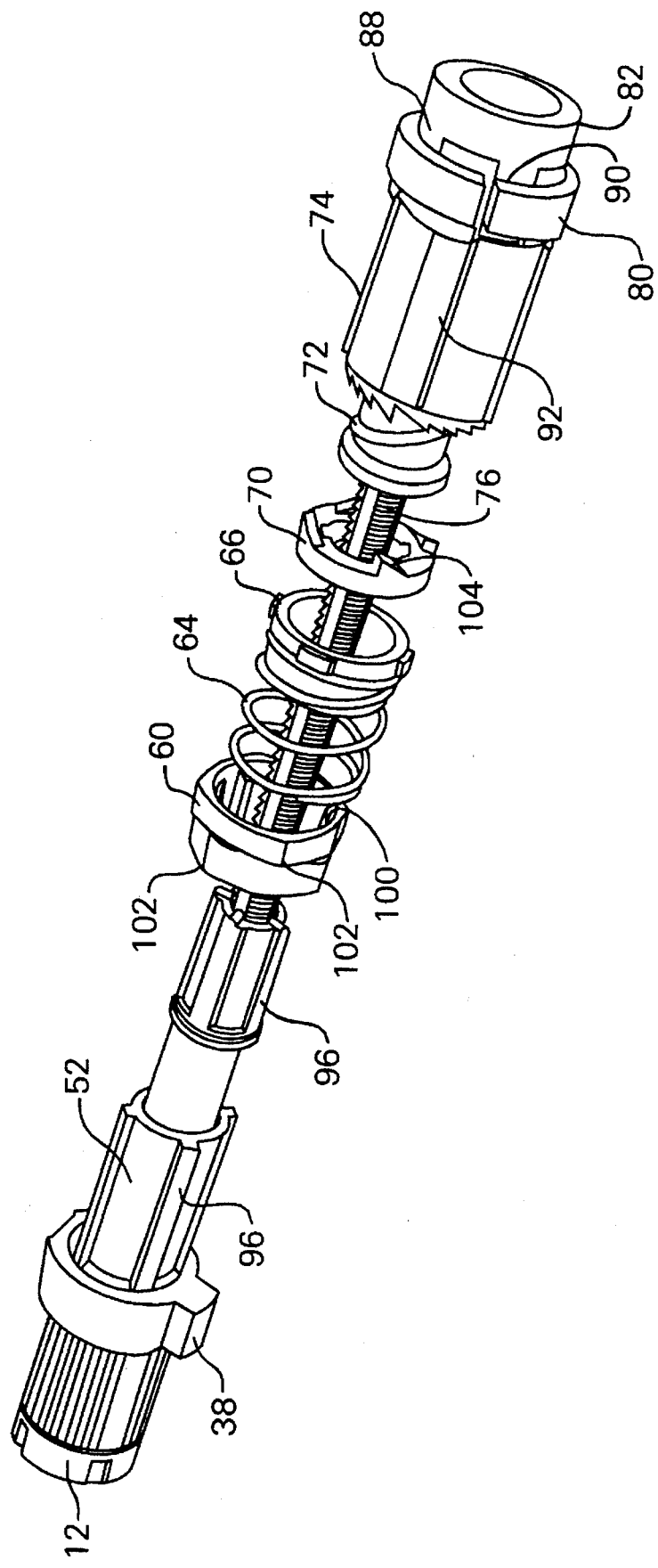
Figure 12:
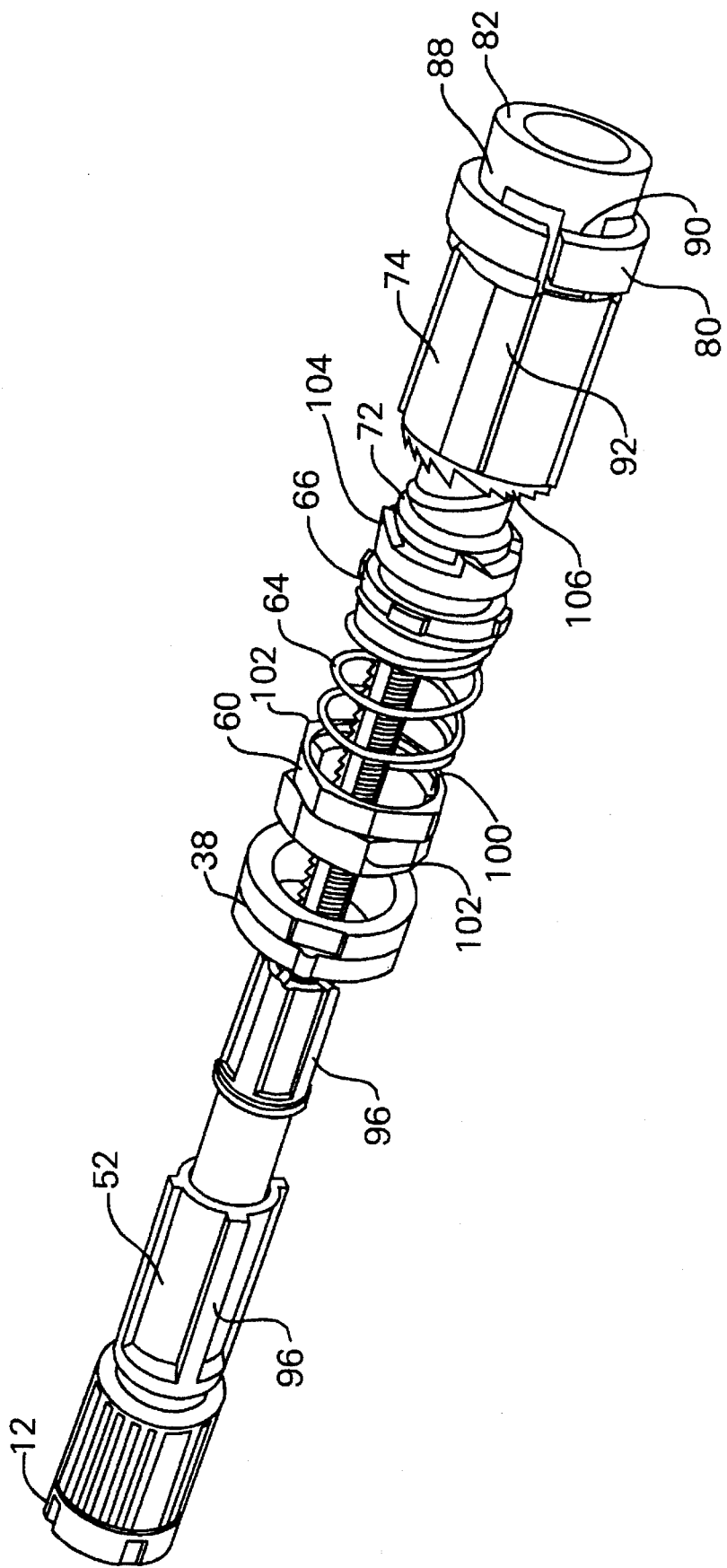
Figure 13:
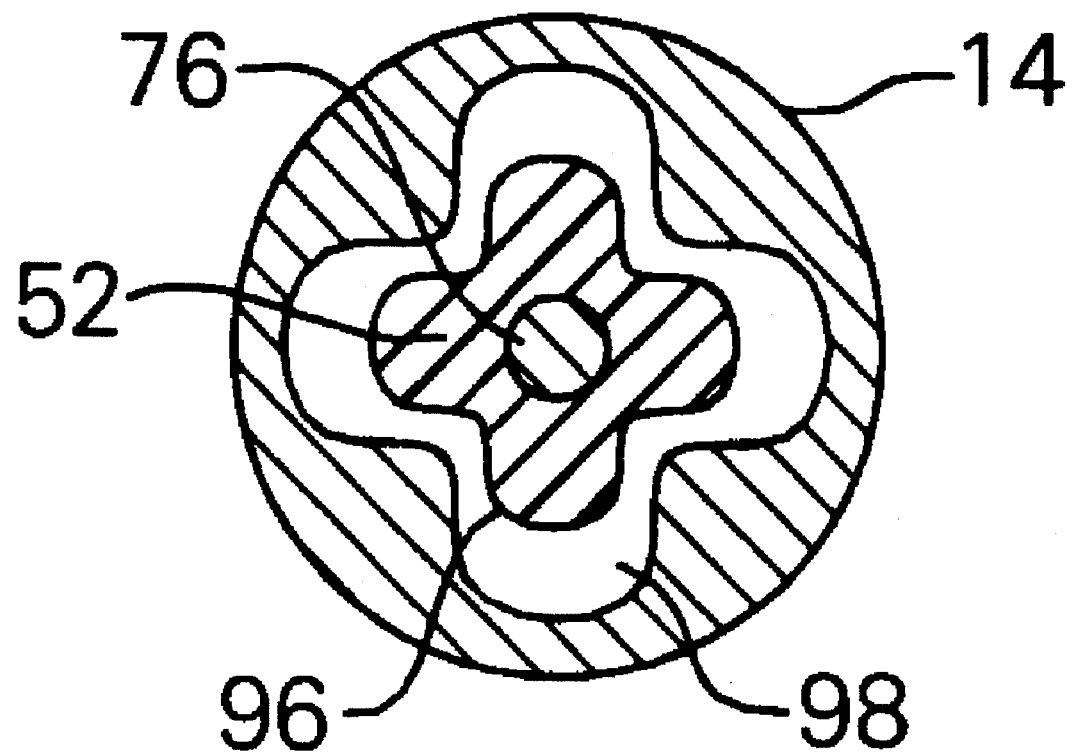
FIG. 13 is a cross-sectional view of the pen-type injector as shown along the line 13—13 in FIG. 6.

FIGS. 5 and 6 show detailed cross-sectional views of a preferred embodiment of a direct drive injection mechanism 20 as shown along the line 5—5 in FIG. 2. FIGS. 7–12 show various perspective views that detail the drive mechanism 20 shown in FIGS. 5 and 6. FIG. 13 is a cross-sectional view of the drive mechanism 20 along the line 13—13 shown in FIG. 6. The drive mechanism 20 includes a dosage knob drive shaft 52, a tension spring 54, a lock nut 56, a display seat 58, an offset camshaft 60, an electronics mount 62, a ratchet spring 64, a ratchet collar 66, a drive calibrator 68, a ratchet gear 70, a synchronizer spring 72, a stationary synchronizer 74, a threaded drive shaft 76, a plunger 78, an end cap 82, a medication cartridge tensioner and synchronizer 82, and a medication cartridge plunger 84 that are coupled as shown in FIGS. 5–12.

The dosage knob drive shaft 52 of the actuator knob 12 is coupled to the threaded drive shaft 76 by a threaded lock nut 56 to secure the actuator knob 12 to the drive shaft 76. The start button 38 is also coupled to the actuator knob 12 by the dosage knob drive shaft 52 to maintain the actuator knob 12 in a depressed position when the pen-type injector 10 is not being used, and to release the actuator knob 12 and activate the microprocessor 32 when the pen-type injector 10 is to be used for an injection. Contained within the actuator knob 12 is a tension spring 54 which is securely attached to the interior of the actuator knob 12. The purpose of the tension spring 54 is to apply pressure to the drive shaft 76 to maintain the drive shaft in a fixed position after each injection and to facilitate movement of the threaded drive shaft 76 toward the medication cartridge 22 during an injection.

The dosage knob drive shaft 52 has splines 96 which, when the actuator knob 12 is in the depressed position, are locked in corresponding spline slots 98 of the injection mechanism housing 14 to prevent the actuator knob, the dosage knob drive shaft 52 and the threaded drive shaft 76 from being rotated. When the actuator knob 12 is released by the start button 38, the actuator knob 12 and the dosage drive shaft 52 move in a direction away from the medication cartridge 22. The splines 96 slide clear of the spline slots 98 so that the actuator knob 12, the dosage knob drive shaft 52 and the threaded drive shaft 76 can be rotated as a single unit to adjust the dosage of medication that will be injected by the pen-type injector 10.

The splines 96 of the dosage drive shaft 52 are also coupled to spline slots 100 of the offset camshaft 60 which is coupled to the counter 40 mounted on the electronics mount 62. The offset camshaft 60 has cam lobes 102 that are in operative contact with the counter 40. When the actuator knob 12 is rotated, the dosage knob drive shaft 52 rotates the offset camshaft 60 and the cam lobes 102 to increment the counter by one count per each predetermined angle of rotation of the actuator knob 12, the dosage knob drive shaft 52, the threaded drive shaft 76 and the offset camshaft 60. In preferred embodiments, the predetermined angle of rotation is 90° (although larger or smaller angles may be used).

The display seat 58 is adapted to hold the display 34 and the microprocessor 32. The microprocessor 32 is coupled to the counter 40 that is mounted on the electronics mount 62 to determine the dosage of medication to be injected based upon the value in the counter 40. The display seat 58 may also be used to hold the clip 36 to allow the pen-type injector 10 to be carried like a pen.

The ratchet spring 64 is permanently attached to the interior of the injection mechanism housing 14. The ratchet spring 64 applies pressure to the ratchet collar 66 which in turn applies pressure to the ratchet gear 70. The ratchet gear 70 has teeth 104 that mate correspondingly with teeth 106 on the stationary synchronizer 74. The synchronizer spring 72 applies a counter pressure on the stationary synchronizer 74 to maintain the ratchet gear 70 and the stationary synchronizer 74 in contact with each other. Thus, when the actuator knob 12 is rotated, a ratchet noise is produced as the ratchet gear 70 is rotated relative to the stationary synchronizer 74. Removal of the medication cartridge 22 reduces the pressure on synchronizer spring 72 so that the corresponding teeth 104 and 106 of the ratchet gear 70 and the stationary synchronizer 74 are disengaged. When the teeth 104 and 106 are disengaged, the actuator knob 12 can be rotated easily with minimal resistance, and the threaded drive shaft 76 can be withdrawn without resistance from the ratchet gear 70.

The stationary synchronizer 74 also has splines 92 which are coupled to corresponding spline slots 94 in the injection mechanism housing 14 to prevent the stationary synchronizer 74 from rotating. However, the splines 92 are slidably coupled to the spline slots 94 so that the stationary synchronizer can slide back and forth within the injection mechanism housing 14. This allows the medication cartridge 22 to increase the tension of the synchronizer spring 72 when the medication cartridge 22 is seated, and this increased tension causes the teeth 104 and 106 to engage.

The drive calibrator 68 is threaded onto the threaded drive shaft 76 to determine the minimum and maximum positions in which the threaded drive shaft 76 can be moved to inject medication from the medication cartridge 22. The drive calibrator 68 also performs as a rotational reference point to keep track of the incremental movement of the threaded drive shaft 76 so that the dosage of medication injected by the pen-type injector can be accurately determined. An end of the drive calibrator 68 has splines 88 that engage corresponding spline slots 90 in the end cap 80 to hold the drive calibrator 68 in a rotationally fixed position. The other side of the end cap 80 is coupled to the medication cartridge tensioner and synchronizer 82 which is used to secure a medication cartridge 22 to the injection housing 14. The threaded drive shaft 76 is coupled to the medication cartridge plunger 84 to inject medication in the medication cartridge 22 when the actuator knob 12 is depressed.

The illustrated direct drive mechanism only requires a single complete depression of the actuator knob 12 to inject different set amounts of medication. The illustrated direct drive allows the user to accurately set various dosage values to be injected. The drive mechanism 20 is capable of providing dosage accuracies of between 0.1 to 1.0 unit increments. However, other dosage increments may be used. Moreover, in alternative embodiments, other suitable drive mechanisms can be used by the pen-type injector such as those disclosed in U.S. Pat. No. 5,114,406 issued May 19, 1992; U.S. Pat. No. 5,226,895 issued Jul. 13, 1993; and U.S. Pat. No. 5,279,585 issued Jan. 18, 1994.

Figure 14:
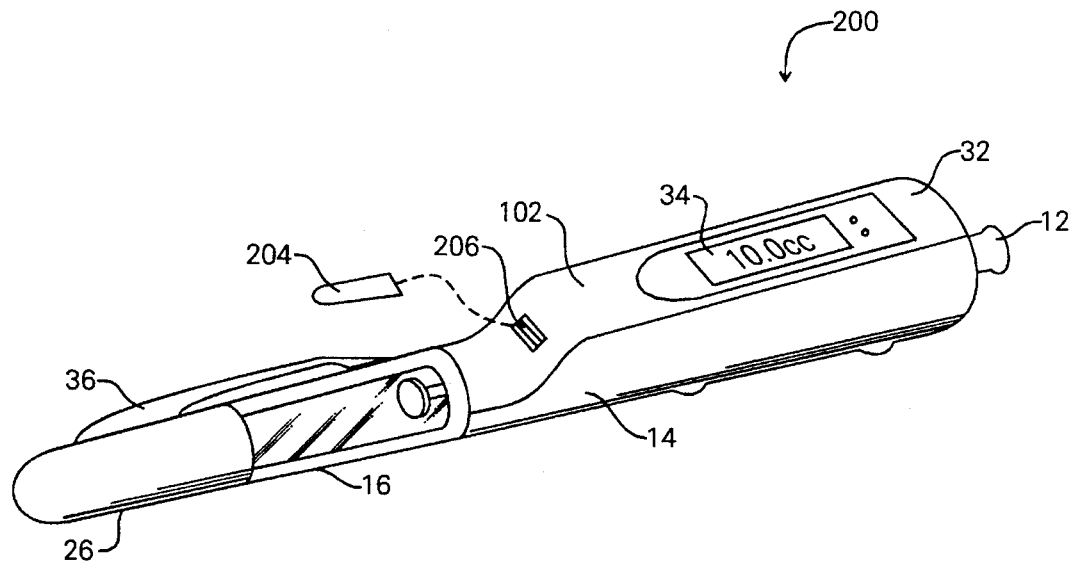
FIG. 14 is a perspective view of a pen-type injector that includes a blood characteristic monitor in accordance with an embodiment of the present invention.
Figure 15:
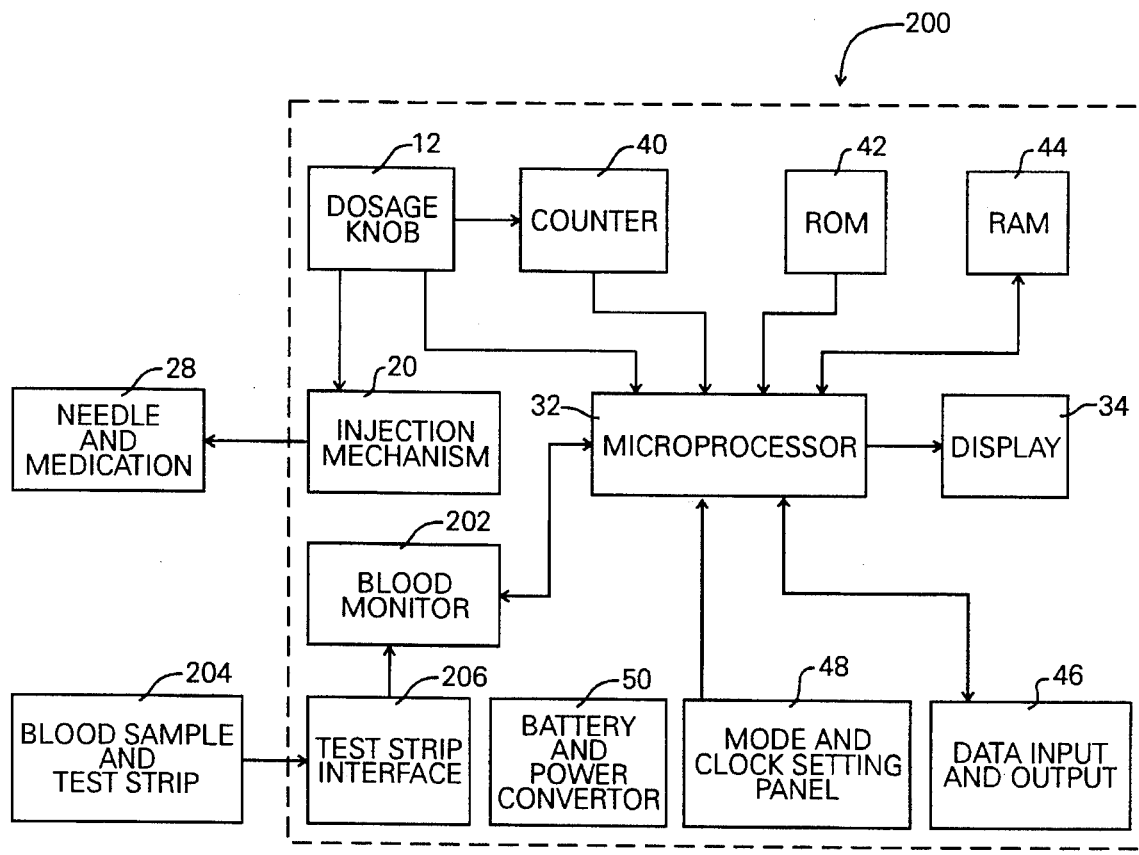
FIG. 15 is a simplified flow block diagram for the pen-type injector with a blood characteristic monitor as shown in FIG. 14.

A pen-type injector 200 in accordance with an embodiment of the present invention is shown in FIGS. 14 and 15. The pen-type injector includes a blood characteristic monitor 202, such as a glucose meter or the like, coupled to the injection mechanism housing 14. This pen-type injector 200, also includes a rotatable actuator knob 12, a medication cartridge housing 16 and a protective needle cover 26 such as those discussed above with respect to the pen-type injector 10. Instead of a window 18, the medication cartridge housing 16 is transparent to allow easy viewing of the medication cartridge 22. Moreover, the clip 36 is located on the protective needle cover 26 rather than the injection mechanism housing 14. The pen-type injector 200 also uses a microprocessor 32 and a display 34. However, in preferred embodiments the display is larger than in the previous embodiment to display more information, and both the display and the microprocessor 32 are coupled to the blood characteristic monitor 202. The pen-type injector 200 with the blood characteristic monitor 202 allows the user to use a single, all-in-one device that keeps records, injects medication, and determines characteristics of a blood sample.

FIG. 15 is a simplified block diagram of the pen-type injector 200 with a blood characteristic monitor 202. The operation of the injection mechanisms and the related components is the same as described above in the previous embodiment. In the pen-type injector 202 the ROM 42 now stores additional programs to operate and control the blood characteristic monitor 202. Moreover, the RAM 44 also stores results obtained from the blood characteristic monitor 202. As shown in FIG. 14, a test strip 204 for holding a blood sample is inserted into the test strip interface 206. This activates the blood characteristic monitor 202 and the microprocessor 32. The blood characteristic monitor 202 analyzes the blood characteristics and sends the analysis results to the microprocessor 32, which displays the results on the display 34 and stores the results in the RAM 44 for later review.

In particular embodiments, the blood characteristic monitor 202 tests for the level of glucose in the blood. Preferably, the blood characteristic monitor 202 uses electro-chemical sensor technology (i.e., the blood sample reacts with a chemical upon the application of an electrical current). The blood characteristic monitor 202 is periodically calibrated by a reusable code strip. To perform the analysis, the blood characteristic monitor utilizes a disposable (one time use) test strip 204. The test strip 204 utilizes capillary action at the end of the test strip to draw in a small amount of blood (typically 3 micro-liters) into a reaction chamber (not shown) in the test strip interface 206 of the blood characteristic monitor 202. When sufficient blood has bee drawn into the reaction chamber, the test sequence begins and a blood glucose reading is displayed on the display 34 in approximately 60 seconds from the start of the testing sequence. In preferred embodiments, the blood characteristic monitor 202 provides blood glucose level results from 40–500 mg/dl (2.2–27.8 mmol/L); however, other ranges may be used.

Operation of the blood characteristic monitor 202 is relatively simple. The operator fully inserts a test strip 204 into the test strip interface 206. This turns on the microprocessor 32 and the blood characteristic monitor 202. In preferred embodiments, the blood analysis mode is activated and the microprocessor 32 causes the display 34 to display the previous test result and the time of the last test event. The previous time and results are alternately flashed for 5 seconds (although longer or shorter times can be used). The user then places a blood sample (usually from a finger) on the end of the inserted test strip 204, and the capillary action in the test strip 204 draws the sample into the reaction chamber of the test strip interface 206. In preferred embodiments, the blood characteristic monitor 202 beeps, or provides some other audible indication, when a sufficient sample has been drawn into the reaction chamber. After the beep, the test is conducted and is typically completed in about 60 seconds. Once the test is completed, the results are displayed on the display 34 and simultaneously stored by the microprocessor 32 in the RAM 44 for later recall. Removal of the test strip 204 automatically turns off the blood characteristic monitor 202 and the microprocessor 32. If the user fails to remove the test strip 204, the microprocessor 32 sounds an alarm, and both the blood characteristic monitor 202 and the microprocessor 32 automatically turn off after 1 minute (although other time periods may be used). In alternative embodiments, other blood characteristic monitors may be used, such as a colormetric blood glucose meter, a dry membrane chemical reaction monitor or the like. Preferred embodiments of the present invention utilize blood characteristic monitors that use electro-chemical sensor techniques developed by Miles Laboratories, Inc.

Figure 16A:
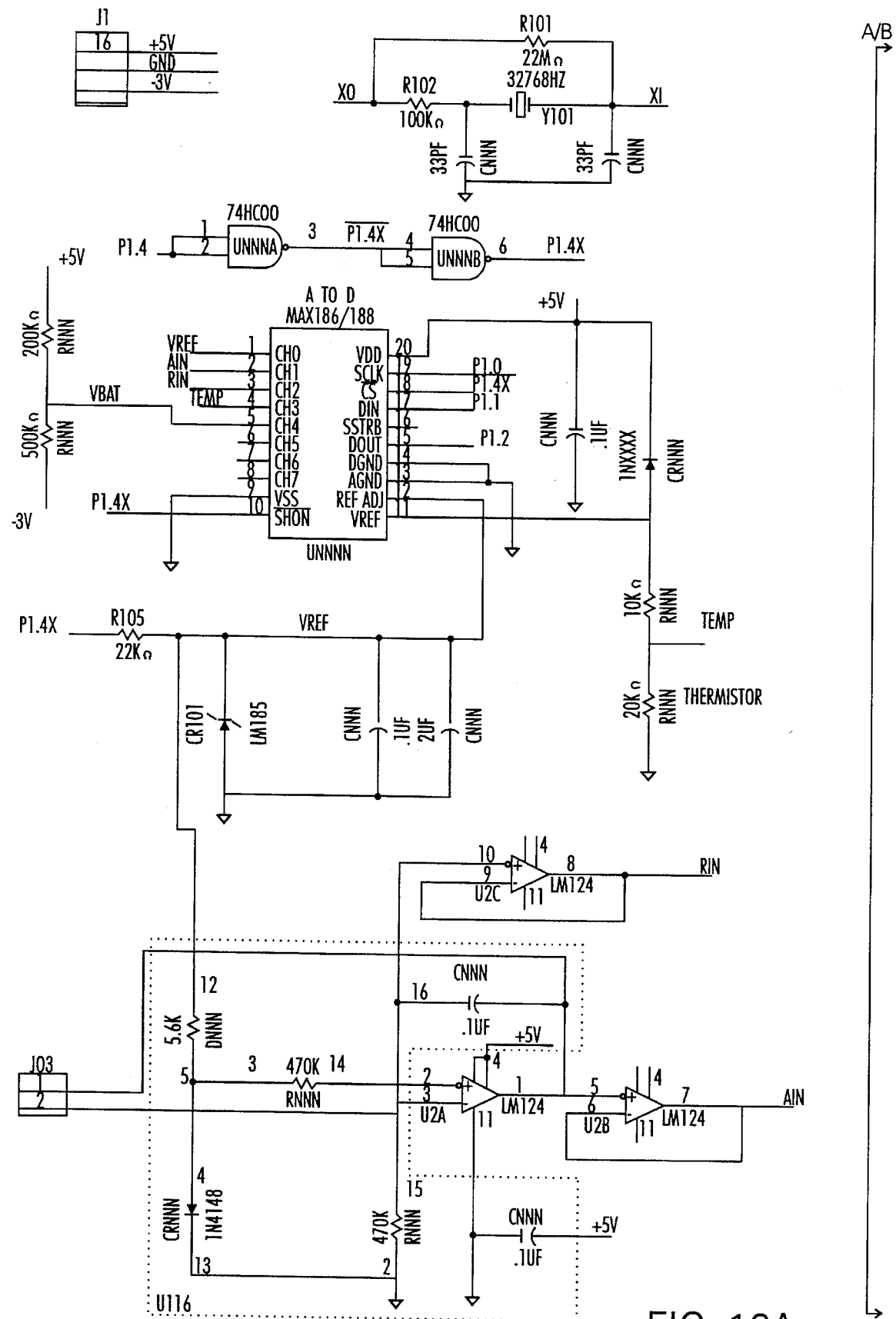
FIGS. 16A and 16B are a circuit schematic for the pen-type injector with a blood characteristic monitor shown in FIGS. 14 and 15.
Figure 16B:
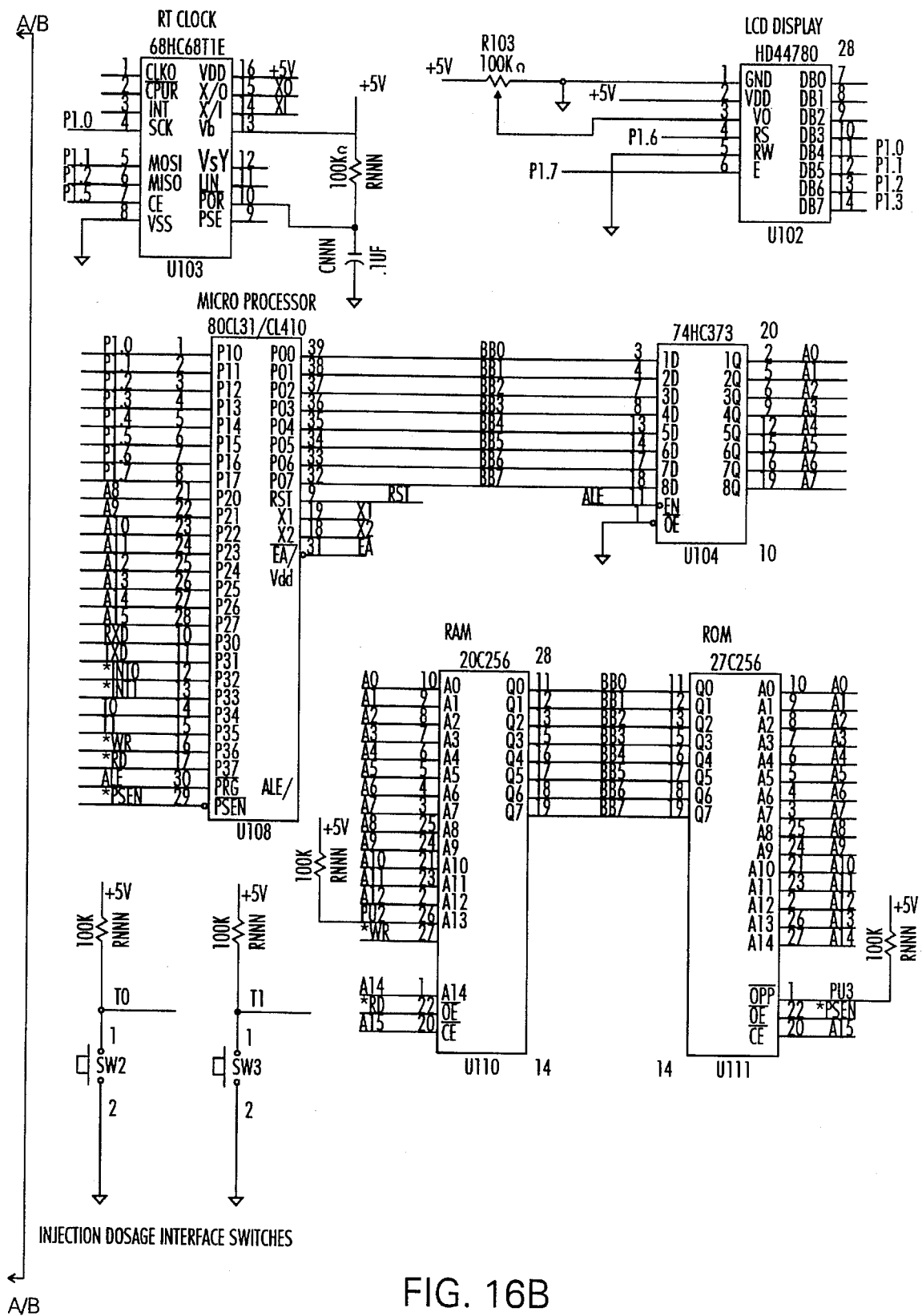

FIGS. 16A and 16B are a circuit schematic showing preferred embodiments of particular circuits used in the pen-type injector 200 with a blood characteristic monitor 202.

FIGS. 17 and 18 show an alternative embodiment of a pen-type injector 250 coupled with a blood characteristic monitor 202. The pen-type injector 250 operates in a manner similar to the embodiments described-above with respect to FIGS. 14–16. However, the test strip interface 206 is 90° offset with respect to the embodiment of FIGS. 14–16, and the display 34 and the mode and clock setting panel 48 are arranged differently. FIG. 18 is a cross-sectional view of the pen-type injector 250 along the line 18—18 shown in FIG. 17. This view illustrates that the pen-type injector 250 can use the drive mechanism 20 described above with respect to the embodiments of FIGS. 1–13. Moreover, FIG. 18 illustrates the relative position of various internal components. For instance, the microprocessor 32, the battery 50, and a reaction chamber 252.

Figure 19:
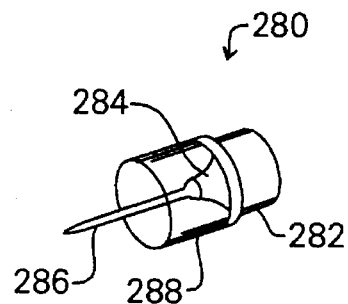
FIG. 19 is a perspective view of a disposable needle in accordance with an embodiment of the present invention.
Figure 20:
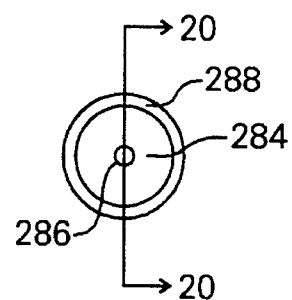
FIG. 20 is an end view of the disposable needle as shown in FIG. 19.
Figure 21:
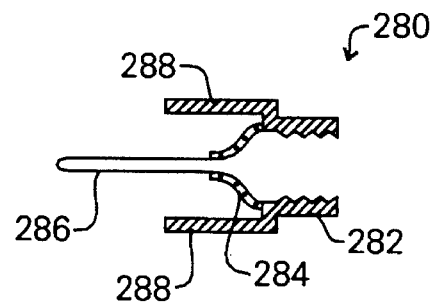
FIG. 21 is a cross-sectional view of the disposable needle as shown along the line 21—21 in FIG. 20.

FIGS. 19–21 show a preferred embodiment of a disposable needle 280 that substantially eliminates or reduces bleeding upon injection. The disposable needle 280 includes a threaded base 282, a needle support 284, a needle portion 286, and a hollow cylindrical cover 288. The threaded needle base 282 is adapted to be coupled to a pen-type injector as described above. However, in alternative embodiments, the needle base 282 may be attached by means of friction or the like, or the disposable needle 280 may be used with injectors other than pen-type injectors. A needle support 284 is coupled to the needle base 282 to hold the needle portion 286. Also coupled to the needle support 284 and the needle base 282 is the hollow cylindrical cover 288. The needle portion 286 is disposed inside the hollow cylindrical cover 288 such that the end of the needle portion 286 coupled to the needle support 284 cannot contact the skin during an injection. This prevents the needle support 284 from spreading the skin at the injection site. Spreading of the skin often results in bleeding. The needle portion 286 extends a sufficient distance beyond the hollow cylindrical cover 288 to allow for the proper administration of an injection. The hollow cylindrical cover helps the user insert the disposable needle 280 to the proper depth beneath the skin for an accurate injection. Moreover, the hollow cylindrical cover 288 tends to press the skin at the injection site together and this substantially eliminates or reduces bleeding at the injection site. The hollow cylindrical cover 288 also makes it easier for the user to attach and remove the disposable needle 280, and decrease the probability of being pricked during attachment and removal of the disposable needle 280.

Figure 22:
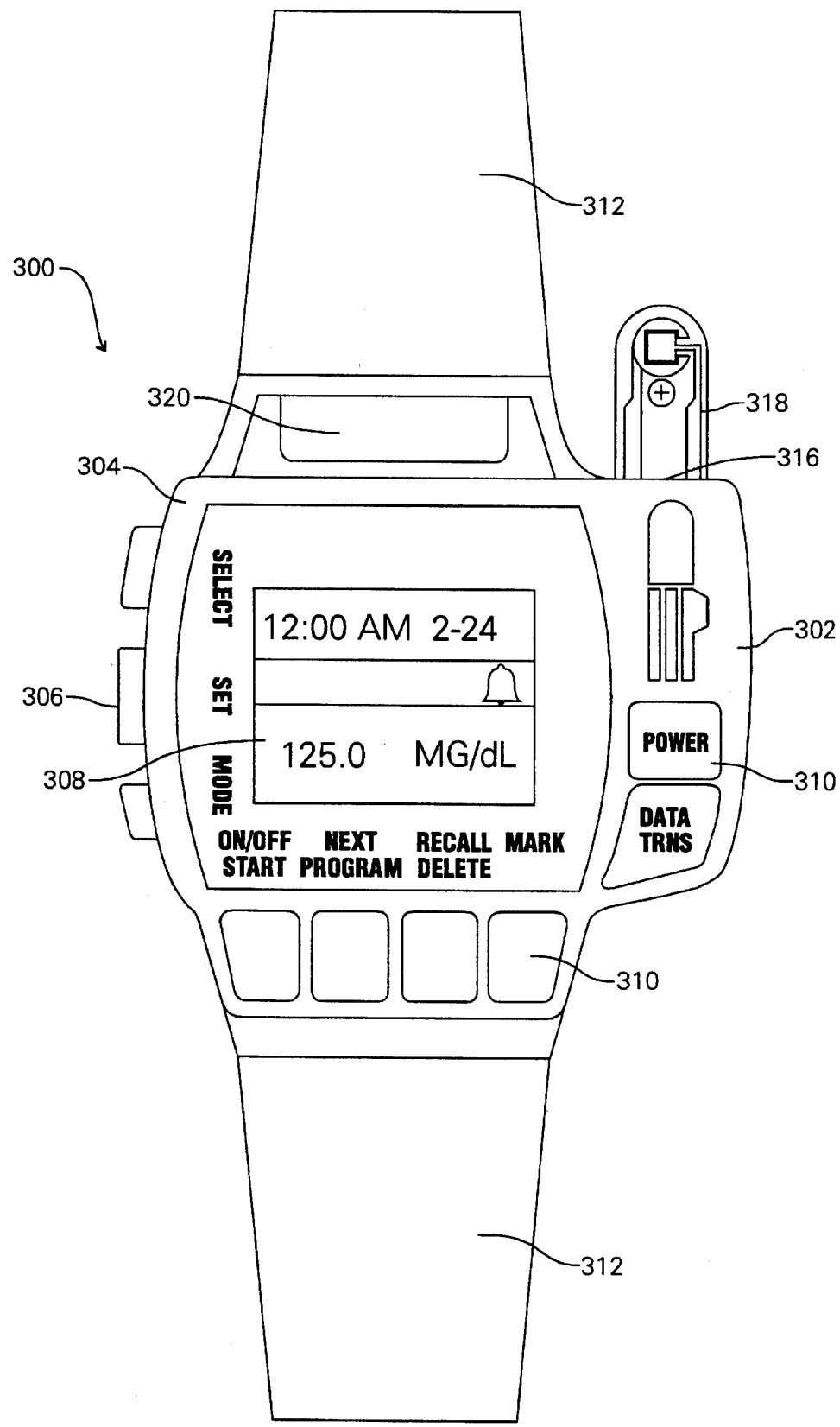
FIG. 22 is a front plan view of a blood characteristic monitor in accordance with an embodiment of the present invention.

FIG. 22 shows a blood characteristic monitor watch 300 in accordance with an embodiment of the present invention. The monitor watch 300 includes a blood characteristic monitor 302 and a wrist watch 304. The blood characteristic monitor 302 is contained with the housing of the wrist watch 304 to provide a portable self-contained blood testing device that is convenient to use and can record detailed blood sample results, as well as injection administration information. This provides detailed reporting that a doctor can use to determine compliance with a prescribed medical regimen.

The wrist watch 304 resembles a conventional LCD watch, in size and shape, and includes a watch setting key pad 306, a display 308, and a function and power/data key pad 310 for controlling the blood characteristic monitor 302. Inside the wrist watch 304 is a microprocessor 314 (see FIG. 23) that couples the key pads 306 and 310 to the blood characteristic monitor 302 and the display 308. The wrist watch 304 is secured to the user's wrist by a pair of watch straps 312.

The blood characteristic monitor 302 includes a test strip interface 316 for receiving and analyzing a test strip 318. The blood characteristic monitor is activated by either insertion of a test strip 318 or the power/data key pad 310. The blood characteristic monitor 302 operates in a manner similar to that described above with respect to the embodiments of FIGS. 14–18. The results of the blood analysis are stored by the microprocessor 314 and may be recalled for later review on the display 308. In particular embodiments, the watch monitor 300 also includes a data input and output (I/O) port 320 which is activated and controlled by the microprocessor 314 and the power/data key pad 310 to upload program instructions and download information stored in a RAM 324 of the watch monitor 300. In preferred embodiments, the data I/O port 320 uses infrared (IR) technology; however, other data port technologies, such as cables or the like, may be used.

Figure 23:
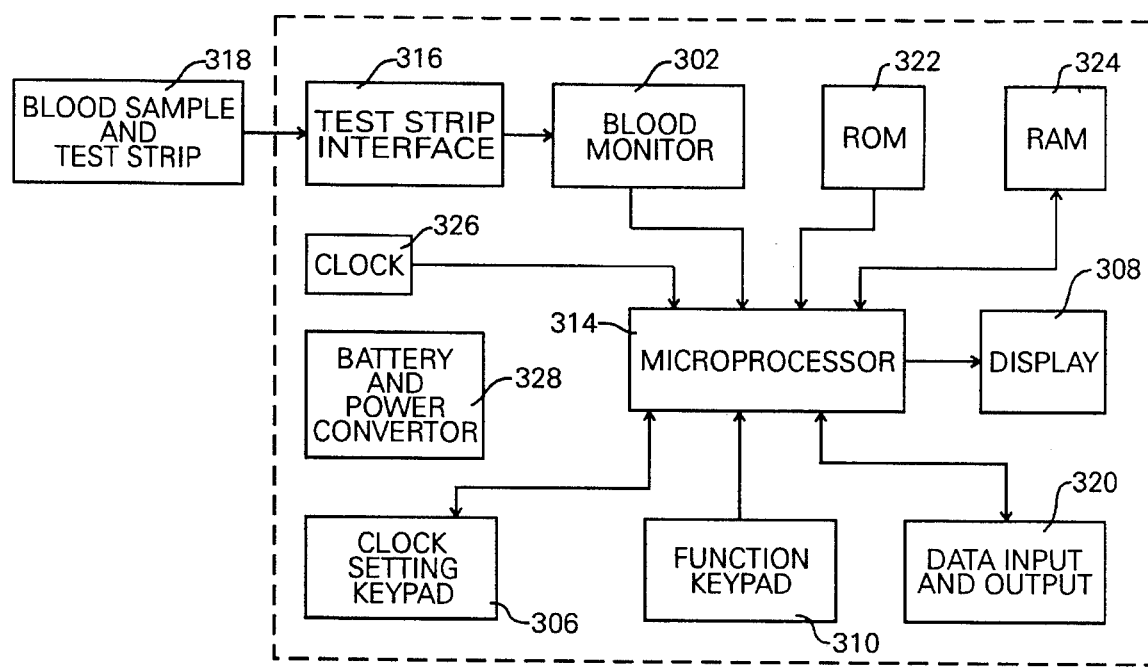
FIG. 23 is a simplified flow block diagram in accordance with the embodiment shown in FIG. 22.

FIG. 23 is a simplified block diagram of the watch monitor 300 with a blood characteristic monitor 302. A test strip 318 is fully inserted into the test strip interface 316 to activate the blood characteristic monitor 302. The blood characteristic monitor 302 analyzes the blood characteristics of the sample and sends the analysis results to the microprocessor 314, which displays the results on the display 308.

The microprocessor 314 is coupled to a ROM 322 and a RAM 324. In preferred embodiments, the ROM 322 is an EPROM and the RAM 324 is a static RAM; however, other comparable memory storage components may be used. The ROM 322 stores the programs used by the microprocessor 314 to determine various parameters, such as the correlation of results and the deviation from preset limits in a medical regimen, the date and the time, and how to report information to the user. The RAM 324 is used by the microprocessor 314 to store information about the blood analysis, as well as injections, for later recall by the user or the doctor. The microprocessor 314 also retrieves information from the RAM 324 so that a user or doctor can transcribe the stored information at a later time to determine compliance with the medical regimen and to spot trends requiring corrective action.

In preferred embodiments, the RAM 324 has a memory capacity for over 100 blood characteristic tests, 100 injection administration events, and memory to keep track of medication scheduling and special events. The microprocessor 314 is programmed to determine trends by comparing dosages administered by injections with the blood analysis results. These trends can be used by the microprocessor 314 to automatically recommend minor changes in the dosages within pre-programmed boundaries set by the doctor, or the trend results can be used by the doctor to directly adjust the dosages boundaries and the programs utilized by the microprocessor 314. This provides the doctor with greater control and flexibility over the user's medical regimen.

In preferred embodiments, the microprocessor 314 is coupled to a data input and output (I/O) port 320, and the user can download the stored information to an external computer (not shown) through the data I/O port 320. The data I/O port 320 is capable of transferring data in both directions so that updated program instructions or reminder alarms can be set by the user or doctor.

A clock setting key pad 306 is also coupled to the microprocessor 314 to provide the user with the capability to store additional information, set the date and the time, or set alarms on an internal clock 326 to indicate when to perform another blood analysis or administer an injection. In alternative embodiments, the microprocessor 314 may perform the internal clock functions without the necessity of a separate internal clock 326. The function key pad 310 also provide the capability to produce detailed reports and to interface with an external computer (not shown). The key pads 306 and 310 are used in conjunction with the display 308 to access the various modes and alarms utilizing methods typically employed to set the time on an LCD watch or the like. In preferred embodiments, the internal clock 326 of the watch monitor 300 is capable of multiple daily alarms, 12/24 hour formatting, and scrolling through a time zone map for easier record keeping during time zone changes.

The watch monitor 300 also includes a self contained battery and power convertor 328. The battery is a small watch type battery, or in preferred embodiments, the battery is a lithium battery capable of providing power for up to 5 years.

In preferred embodiments, the blood characteristic monitor 302 analyses a blood sample to determine the level of glucose in the blood and the blood characteristic monitor 302 uses an electro-chemical sensor technology such as described above with respect to the embodiments of FIGS. 14–18. A disposable (one time use) test strip 318 uses capillary action at the end of the test strip 318 to draw in a small amount of blood (typically 3 microliters) into a reaction chamber (not shown) of the test strip interface 316. When sufficient blood has been drawn into the reaction chamber, the testing sequence begins and a blood glucose reading is displayed on the display 308 in approximately 60 seconds from the start of the testing sequence. The blood characteristic monitor 302 provides blood glucose results from 40–500 mg/dl (2.2–27.8 mmol/L); however, other ranges may be used.

The blood characteristic monitor 302 is operated in substantially the same manner as described above with respect to the embodiments of FIGS. 14–18. The operator fully inserts the test strip 318 into the test strip interface 316 to turn on the blood characteristic monitor 302 and access the microprocessor 314. The blood characteristic analysis mode is activated and the microprocessor 314 causes the display 308 to display the previous test result and the time of the last test event. The user then places a blood sample (usually from a finger) on the end of the inserted test strip 318 which draws the sample into the reaction chamber of the test strip interface 316. In preferred embodiments, the blood monitor 302 beeps, or provides some other audible indication, when a sufficient sample has been drawn into the reaction chamber. After the beep, the test is conducted and is typically completed in about 60 seconds. Once the test is completed, the results are displayed on the display 308 and simultaneously stored by the microprocessor 314 in the RAM 324 for later recall. Removal of the test strip 318 automatically turns off the blood monitor 302 and returns the microprocessor 314 and the watch monitor 300 to the watch mode. If the user fails to remove the test strip 318, the microprocessor 314 sounds an alarm, and the blood monitor 302 is automatically turned off after 1 minute (although other time periods may be used). In alternative embodiments, other blood characteristic monitors may be used, such as a colormetric blood glucose meter, a dry membrane chemical reaction monitor or the like. Preferred embodiments utilize the above-described electro-chemical sensor technology in sensors produced by Miles Laboratories, Inc.

FIGS. 24(a)–24(d) illustrate typical reports that can be obtained via the data I/O port 320 from the watch monitor 300. FIG. 24(a) shows a summary report of the blood analysis performed by the blood characteristic monitor 302. The readings are broken down into at least four basic time frames: breakfast, lunch, diner and snack. In preferred embodiments, the time frames may be further broken down into pre and post time frames. The report lists the number of blood analysis readings in each time frame, the standard deviation and the average value for the analyzed blood samples. FIG. 24(b) shows a detailed report of all the individual blood analysis events. The report provides the date, the day, the time and the results for each analyzed blood sample. Thus, this portion of the report allows the doctor or user to spot anomalous readings. FIG. 24(c) shows a detailed report on injections that have been administered and recorded by the user. The report provides the date, the day and the time of the injection. The report also recites how much of each type of insulin (regular (R) or intermediate (L)) was injected. This provides the doctor or user with information to compare blood analysis results with the amount of medication administered in the injection. FIG. 24(d) shows a detailed report on markers that are set and recorded by the user to indicate certain events or changes from the regular medical regimen. This provides the doctor or user with information that can aid in understanding and correlating otherwise anomalous results.

In preferred embodiments, test results can be deleted by pressing the delete button on the function key pad 310. This removes the results from the blood test average, for calibration or control test results, to prevent skewing the actual analysis information. The marker key on the function keypad 310 gives the user the option to store important information along with results already stored in the RAM 324. This can aid the user in recalling specific events or types of events that establish a trend. The marks are inserted by pressing the mark key and turning the blood characteristic monitor 302 off. Markers can be used to identify meal times, exercise times, injection events, or special circumstances and changes from the normal regimen.

In alternative embodiments, the watch monitor 300 can be used with a pen-type injector 10 described in the embodiment discussed above with respect to FIGS. 1–13. The data I/O port 320 of the watch monitor 300 can be utilized to download the injection information stored in the RAM 44 of the pen-injector 10. This simplifies the input of relevant injection data into the watch monitor 300.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A medical injection device, comprising:
    an injection mechanism including an actuator for setting the dosage and administering an injection of a medication contained within the injection device;
    a processor coupled to the actuator of the injection mechanism to determine a value equal to the dosage set by the actuator of the injection mechanism; and
    a memory device coupled to the processor to store the value equal to the dosage determined by the processor along with other values corresponding to previously injected dosages for later recall.

2. A device according to claim 1, further including a receptacle capable of holding the medication, wherein the injection mechanism further includes a drive mechanism coupled between the actuator and the receptacle to inject the set dosage of the medication, and wherein the actuator of the injection mechanism triggers the drive mechanism to administer the injection of the medication held in the receptacle.

3. A device according to claim 1, further including a display device coupled to the processor to display the value equal to the dosage determined by the processor.

4. A device according to claim 3, further including a clock circuit coupled to the processor for determining the time, wherein the time is stored in the memory device with the value equal to the dosage determined by the processor, and wherein the time is displayed on the display device.

5. A device according to claim 4, wherein the clock circuit further includes means to determine the date.

6. A device according to claim 4, wherein the clock circuit further includes means to provide an alarm indication at a predetermined time.

7. A device according to claim 1, further including a data port coupled to the processor that is used to transfer the value equal to the dosage stored in the memory device to an external data collection device.

8. A device according to claim 7, wherein the data port is used to transfer program instructions from an external programming device to the microprocessor.

9. A medical device, comprising:
   a medication injector for injecting a dosage of a medication;
   a blood characteristic monitor for analyzing a blood sample;
   a processor coupled to the medication injector and the blood characteristic monitor, wherein the processor determines a value equal to the dosage of the medication to be injected by the medication injector, and wherein the processor determines blood characteristics from the blood sample analyzed by the blood characteristic monitor.

10. A device according to claim 9, further including a memory device coupled to the processor to store the value equal to the dosage and the blood characteristics determined by the processor.

11. A device according to claim 10, further including a receptacle capable of holding the medication and an injection mechanism having an actuator knob for setting the dosage of the medication to be administered by the medication injector and a drive mechanism coupled between the actuator knob and the receptacle to inject the set dosage of the medication, wherein the actuator knob of the injection mechanism triggers the drive mechanism to administer the injection of the medication held in the receptacle.

12. A device according to claim 10, further including a display device coupled to the processor to display the value equal to the dosage and the blood characteristics determined by the processor.

13. A device according to claim 12, further including a clock circuit coupled to the processor for determining a time, wherein the time is stored in the memory device with the value equal to the dosage and the blood characteristics determined by the processor, and wherein the time is displayed on the display device.

14. A device according to claim 13, wherein the clock circuit further includes means to determine the date.

15. A device according to claim 13, wherein the clock circuit further include means to provide an alarm indication at a predetermined time.

16. A device according to claim 10, further including a data port coupled to the processor that is used to transfer the value equal to the dosage stored in the memory device to an external data collection device.

17. A device according to claim 9, further including a data port coupled to the processor that is used to transfer program instructions from an external programming device to the processor.

18. A device according to claim 9, further including a clock and a memory storage device coupled to the processor for storing a measure of time from the clock and the blood characteristics determined by the processor.

19. A device according to claim 18, further including a display device coupled to the processor to display the measure of the time from the clock and the blood characteristics determined by the processor.

20. A device according to claim 18, further including a data port coupled to the processor that is used to transfer the measure of the time and the blood characteristics stored in the memory device to an external data collection device.

21. A device according to claim 20, wherein the data port uses infrared energy to transfer the measure of the time and the blood characteristics stored in the memory storage device.

22. A device according to claim 9, further including a data port coupled to the processor that is used to transfer program instructions from an external programing device to the processor.

23. A device according to claim 22, wherein the data port uses infrared energy to transfer the program instructions.

24. A portable blood monitor, comprising:
   a housing sized and adapted to be worn on a wrist;
   a clock contained in the housing for measuring time;
   a blood characteristic monitor contained in the housing for analyzing a blood sample; and
   a processor coupled to the blood characteristic monitor and the clock, wherein the processor determines blood characteristics based on the analyzed blood sample from the blood characteristic monitor, and wherein the processor uses the measure of the time from the clock to identify when the blood characteristics were determined.

25. A monitor according to claim 24, further including a memory storage device coupled to the processor for storing the measure of time from the clock and the blood characteristics determined by the processor.

26. A monitor according to claim 25, further including a display device coupled to the processor to display the measure of the time from the clock and the blood level characteristics determined by the processor.

27. A monitor according to claim 25, further including a data port coupled to the processor that is used to transfer measure of the time and the blood characteristics stored in the memory device to an external data collection device.

28. A monitor according to claim 24, wherein the clock circuit further includes means to determine the date.

29. A monitor according to claim 24, wherein the clock circuit further includes means to provide an alarm indication at a predetermined time.

30. A monitor according to claim 24, further including a data port coupled to the processor that is used to transfer program instructions from an external programming device to the processor.

31. A monitor according to claim 30, wherein the data port uses infrared energy to transfer the measure of the time and the blood characteristics.

32. A monitor according to claim 30, wherein the data port uses infrared energy to transfer the program instructions.

33. A portable medical device to maintain and monitor a condition of an individual's body, the device comprising:
   an injector for injecting a dosage of an injectable substance into the individual's body;
   a characteristic monitor for analyzing a fluid sample consisting of saliva, urine or blood removed from the individual's body;
   a processor coupled to the injector and the characteristic monitor, wherein the processor determines a value equal to the dosage of the injectable substance to be injected by the injector into the individual's body, and wherein the processor determines sample characteristics from the sample analyzed by the characteristic monitor.

34. A device according to claim 33, further including a memory device coupled to the processor to store the value equal to the dosage and the sample characteristics determined by the processor.

35. A device according to claim 34, further including a receptacle capable of holding the injectable substance and an injection mechanism having an actuator knob for setting the dosage of the injectable substance to be administered by the injector and a drive mechanism coupled between the actuator knob and the receptacle to inject the set dosage of the injectable substance, wherein the actuator knob of the injection mechanism triggers the drive mechanism to administer the injection of the injectable substance held in the receptacle.

36. A device according to claim 34, further including a display device coupled to the processor to display the value equal to the dosage and the sample characteristics determined by the processor.

37. A device according to claim 36, further including a clock circuit coupled to the processor for determining a time, wherein the time is stored in the memory device with the value equal to the dosage and the sample characteristics determined by the processor, and wherein the time is displayed on the display device.

38. A device according to claim 37, wherein the clock circuit further includes means to determine the date.

39. A device according to claim 37, wherein the clock circuit further includes means to provide an alarm indication at a predetermined time.

40. A device according to claim 34, further including a data port coupled to the processor that: is used to transfer the value equal to the dosage stored in the memory device to an external data collection device.

41. A device according to claim 33, further including a data port coupled to the processor that is used to transfer program instructions from an external programming device to the processor.

42. A device according to claim 33, further including a clock and a memory storage device coupled to the processor for storing a measure of time from the clock and the sample characteristics determined by the processor.

43. A device according to claim 42, further including a display device coupled to the processor to display the measure of the time from the clock and the sample characteristics determined by the processor.

44. A device according to claim 42, further including a data port coupled to the processor that is used to transfer the measure of the time and the sample characteristics stored in the memory device to an external data collection device.

45. A device according to claim 44, wherein the data port uses infrared energy to transfer the measure of the time and the sample characteristics stored in the memory device.

46. A device according to claim 33, further including a data port coupled to the processor that is used to transfer program instructions from an external programming device to the processor.

47. A device according to claim 46, wherein the data port uses infrared energy to transfer the program instructions.

48. A method of maintaining and monitoring a condition of an individual's body with a portable medical device, the method comprising the steps of:

determining a value equal to a dosage of an injectable substance to be injected into the individual's body using a processor in the medical device;

injecting a dosage of a the injectable substance into the individual's body using an injector in the medical device;

removing a fluid sample consisting of saliva, urine or blood removed from the individuals body;

analyzing a sample with a characteristic monitor in the medical device;

determining sample characteristics from the sample analyzed by the characteristic monitor with the processor in the medical device.

49. A method according to claim 48, further including the step of transferring program instructions from an external programming device to the processor.

50. A method according to claim 48, further including the step of storing the value equal to the dosage and the sample characteristics determined by the processor in a memory device.

51. A method according to claim 50, further including the step of transferring the value equal to the dosage stored in the memory device to an external data collection device.

52. A method according to claim 50, further including the step of displaying the value equal to the dosage and the sample characteristics determined by the processor.

53. A method according to claim 52, further including the steps of:

determining a time;

storing the time in the memory device with the value equal to the dosage and the sample characteristics determined by the processor; and displaying the time.

54. A method according to claim 53, further including the step of determining the date.

55. A method according to claim 54, further including the step of providing an alarm indication at a predetermined time.

* * * * *

(12) EX PARTE REEXAMINATION CERTIFICATE (5929th)
United States Patent
Castellano et al.

(10) Number: US 5,536,249 C1
(45) Certificate Issued: *Oct. 9, 2007

(54) PEN-TYPE INJECTOR WITH A MICROPROCESSOR AND BLOOD CHARACTERISTIC MONITOR

(75) Inventors: Thomas P. Castellano, Los Angeles, CA (US); Robert Schumacher, Beverly Hills, CA (US)

(73) Assignee: Visionary Medical Products, Inc., Los Angeles, CA (US)

Reexamination Request:
No. 90/007,547, May 18, 2005

Reexamination Certificate for:
Patent No.: 5,536,249
Issued: Jul. 16, 1996
Appl. No.: 08/208,636
Filed: Mar. 9, 1994

( * ) Notice: This patent is subject to a terminal disclaimer.

(51) Int. Cl.
*A61M 31/00* (2006.01)

(52) U.S. Cl. .................................. 604/65; 128/DIG. 1
(58) Field of Classification Search .................... 604/65
See application file for complete search history.

(56) References Cited

U.S. PATENT DOCUMENTS

| | | | |
|---|---|---|---|
| 1,997,129 A | 4/1935 | Taylor et al. | |
| 2,221,739 A | 11/1940 | Reiter | |
| 2,605,763 A | 8/1952 | Smoot | |
| 2,632,445 A | 3/1953 | Kas | |
| 2,695,023 A | 11/1954 | Brown | |
| 2,718,299 A | 9/1955 | Atwater et al. | |
| 3,110,310 A | 11/1963 | Cislak | |
| 3,141,583 A | 7/1964 | Mapel et al. | |
| 3,293,749 A | 12/1966 | George et al. | |
| 3,348,545 A | 10/1967 | Sarnoff et al. | |
| 3,481,510 A | 12/1969 | Allen, Jr. | |
| 3,517,668 A | 6/1970 | Brickson | |
| 3,583,399 A | 6/1971 | Ritsky | |
| 3,894,683 A | 7/1975 | Carhart et al. | |
| 3,923,060 A | 12/1975 | Ellinwood, Jr. | ............. 128/260 |

(Continued)

FOREIGN PATENT DOCUMENTS

| | | |
|---|---|---|
| CA | 1103314 | 6/1981 |
| CH | 1293302 | 9/1953 |
| DE | 730971 | 12/1942 |
| DE | 70784 | 12/1959 |
| DE | 22140 | 10/1961 |
| DE | 3824217 | 1/1990 |
| EP | 0 037 696 | 10/1981 |
| EP | 0 058 536 | 8/1982 |
| EP | 0098592 | 7/1983 |
| EP | 0 143 895 | 6/1985 |

(Continued)

OTHER PUBLICATIONS

Opposition to European Patent No. 749,332, filed on behalf of Novo Nordisk A/S and communicated to the patentee Apr. 4, 2006.

*Primary Examiner*—Beverly M. Flanagan

(57) ABSTRACT

A medical injection device, such as a pen-type injector has a microprocessor coupled to the injector that records the date, the time, and the amount of each injection. The microprocessor may also be coupled to a display to indicate the amount of medication to be injected. The medical injection device can also be coupled with a blood characteristic monitor to analyze characteristics of the blood. This provides a single, all-in-one device that performs a variety of functions, and requires only a minimum of space. The medical injection device may also use a disposable needle that substantially eliminates or reduces bleeding from an opening in the skin at the injection site.

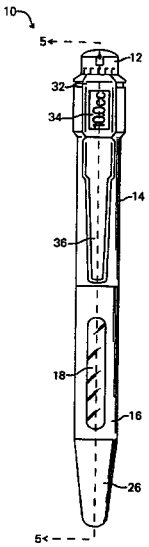

U.S. PATENT DOCUMENTS

| | | |
|---|---|---|
| 3,977,574 A | 8/1976 | Thomas |
| 4,003,379 A | 1/1977 | Ellinwood, Jr. ............. 128/260 |
| 4,022,207 A | 5/1977 | Citrin |
| 4,099,548 A | 7/1978 | Sturm et al. |
| 4,146,029 A | 3/1979 | Ellinwood, Jr. ............. 128/260 |
| 4,333,458 A | 6/1982 | Margulies et al. |
| 4,395,921 A | 8/1983 | Oppenlander |
| 4,413,760 A | 11/1983 | Paton |
| 4,415,101 A | 11/1983 | Shapiro et al. |
| 4,425,121 A | 1/1984 | Young et al. |
| 4,435,173 A | 3/1984 | Siposs et al. |
| 4,444,560 A | 4/1984 | Jacklich |
| 4,457,712 A | 7/1984 | Dragan |
| 4,470,317 A | 9/1984 | Sabloewski et al. |
| 4,475,905 A | 10/1984 | Himmelstrup |
| 4,498,904 A | 2/1985 | Turner et al. |
| 4,526,294 A | 7/1985 | Hirschmann et al. |
| 4,526,569 A | 7/1985 | Bernardi ..................... 604/4 |
| 4,529,401 A | 7/1985 | Leslie et al. |
| 4,581,022 A | 4/1986 | Leonard et al. |
| 4,592,745 A | 6/1986 | Rex et al. |
| 4,627,445 A | 12/1986 | Garcia et al. ............... 128/770 |
| 4,633,878 A | 1/1987 | Bombardieri ............... 128/635 |
| 4,659,327 A | 4/1987 | Bennett et al. |
| 4,664,128 A | 5/1987 | Lee |
| 4,710,172 A | 12/1987 | Jacklich et al. |
| 4,710,178 A | 12/1987 | Henri et al. |
| 4,731,726 A | 3/1988 | Allen, III ................... 364/416 |
| 4,820,287 A | 4/1989 | Leonard |
| 4,865,591 A | 9/1989 | Sams |
| 4,883,472 A | 11/1989 | Michel |
| 4,936,833 A | 6/1990 | Sams |
| 4,950,246 A | 8/1990 | Muller |
| 4,953,552 A | 9/1990 | DeMarzo ..................... 128/635 |
| 4,959,056 A | 9/1990 | Dombrowski et al. |
| 4,959,196 A | 9/1990 | Moisson .................. 422/82.05 |
| 4,998,570 A | 3/1991 | Strong |
| 5,024,656 A | 6/1991 | Gasaway et al. |
| 5,050,612 A * | 9/1991 | Matsumura ................. 600/483 |
| 5,069,668 A | 12/1991 | Boydman |
| 5,085,642 A | 2/1992 | Sarnoff et al. |
| 5,092,842 A | 3/1992 | Bechtold et al. |
| 5,097,834 A | 3/1992 | Skrabal ....................... 128/632 |
| 5,102,393 A | 4/1992 | Sarnoff et al. |
| 5,104,380 A | 4/1992 | Holman et al. |
| 5,112,317 A | 5/1992 | Michel |
| 5,114,406 A | 5/1992 | Gabriel et al. |
| 5,139,484 A | 8/1992 | Hazon et al. |
| 5,176,632 A | 1/1993 | Bernardi ...................... 604/66 |
| 5,180,371 A | 1/1993 | Spinello |
| 5,226,895 A | 7/1993 | Harris |
| 5,226,896 A | 7/1993 | Harris |
| 5,243,982 A | 9/1993 | Mostl et al. ................. 128/632 |
| 5,244,461 A | 9/1993 | Derlien |
| 5,244,465 A | 9/1993 | Michel |
| 5,279,585 A | 1/1994 | Balkwill |
| 5,279,586 A | 1/1994 | Balkwill |
| 5,343,869 A * | 9/1994 | Pross et al. .................. 600/301 |
| 5,364,346 A | 11/1994 | Schrezenmeir ............... 604/50 |
| 5,383,865 A | 1/1995 | Michel |
| 5,497,772 A * | 3/1996 | Schulman et al. .......... 600/347 |
| 5,522,805 A * | 6/1996 | Vancaillie et al. .......... 604/246 |
| 5,593,390 A * | 1/1997 | Castellano et al. ......... 604/187 |
| 5,728,074 A * | 3/1998 | Castellano et al. ......... 604/207 |
| 5,925,021 A * | 7/1999 | Castellano et al. ......... 604/207 |

FOREIGN PATENT DOCUMENTS

| | | |
|---|---|---|
| EP | 0 416 975 | 3/1991 |
| EP | 0 225 137 | 6/1991 |
| EP | 0 249 687 | 6/1993 |
| FR | 1 149 735 | 12/1957 |
| FR | 1 170 312 | 1/1959 |
| FR | 1 445 659 | 6/1966 |
| FR | 2 148 642 | 9/1979 |
| FR | 2 557 445 | 5/1985 |
| GB | 1 225 495 | 3/1971 |
| GB | 1574267 | 9/1980 |
| GB | 2 109 690 | 2/1982 |
| JP | 5-49696 | 3/1993 |
| WO | WO 85/02546 | 6/1985 |
| WO | WO 86/01728 | 3/1986 |
| WO | 92/13583 | 8/1992 |
| WO | 87/03814 | 7/1998 |
| WO | 88/05643 | 8/1998 |

* cited by examiner

© US 5,536,249 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 7, 9, 22, 24, 33, and 48 are determined to be patentable as amended.

Claims 2–6, 8, 10–21, 23, 25–32, 34–47, and 49–55 dependent on an amended claim, are determined to be patentable.

1. A *pen-type* medical injection device, comprising *in a single hand held housing*:
   an injection mechanism including an actuator *manipulated by the user* for setting the dosage and administering an injection of a medication contained within the injection device;
   a processor coupled to the actuator of the injection mechanism to determine a value equal to the dosage set by the actuator of the injection mechanism; and
   a memory device coupled to the processor to store the value equal to the dosage determined by the processor along with other values corresponding to previously injected dosages for later recall.

7. A device according to claim 1, further including a data port coupled to the processor that is used to transfer the *numerical* value equal to the dosage stored in the memory device to an external data collection device.

9. A medical device, comprising:
   a medication injector for injecting a dosage of a medication;
   a blood characteristic monitor for analyzing a *non-perfusate* blood sample;
   a processor coupled to the medication injector and the blood characteristic monitor, wherein the processor determines a value equal to the dosage of the medication to be injected by the medication injector, and wherein the processor determines blood characteristics from the *non-perfusate* blood sample analyzed by the blood characteristic monitor.

22. A device according to claim 9, further including a data port coupled to the processor that is used to transfer program instructions from an external [programing] *programming* device to the processor.

24. A portable blood monitor, comprising:
   a housing sized and adapted to be worn on a wrist;
   a clock contained in the housing for measuring time;
   a blood characteristic monitor contained in the housing for analyzing a *non-perfusate* blood sample; and
   a processor coupled to the blood characteristic monitor and the clock, wherein the processor determines blood characteristics based on the analyzed *non-perfusate* blood sample from the blood characteristic monitor, and wherein the processor uses the measure of the time from the clock to identify when the blood characteristics were determined.

33. A portable medical device to maintain and monitor a condition of an individual's body, the device comprising:
   an injector for injecting a dosage of an injectable substance into the individual's body;
   a characteristic monitor for analyzing a *non-perfusate* fluid sample consisting of [saliva, urine or] blood removed from the individual's body;
   a processor coupled to the injector and the characteristic monitor, wherein the processor determines a value equal to the dosage of the injectable substance to be injected by the injector into the individual's body, and wherein the processor determines sample characteristics from the *non-perfusate* sample analyzed by the characteristic monitor.

48. A method of maintaining and monitoring a condition of an individual's body with a portable medical device, the method comprising the steps of:
   determining a value equal to a dosage of an injectable substance to be injected into the individual's body using a processor in the medical device;
   injecting a dosage of [a] *the* injectable substance into the individual's body using an injector in the medical device;
   removing a *non-perfusate* fluid sample consisting of [saliva, urine or] blood removed from the individuals body;
   analyzing [a] *the non-perfusate* sample with a characteristic monitor in the medical device;
   determining sample characteristics from the *non-perfusate* sample analyzed by the characteristic monitor with the processor in the medical device.

* * * * *